(12) United States Patent
Taheri

(10) Patent No.: US 7,854,758 B2
(45) Date of Patent: Dec. 21, 2010

(54) EXCLUSION OF ASCENDING/DESCENDING AORTA AND/OR AORTIC ARCH ANEURYSM

(76) Inventor: Syde A. Taheri, 9095 Main St., Williamsville, NY (US) 14031

( * ) Notice: Subject to any disclaimer, the term of this patent is extended or adjusted under 35 U.S.C. 154(b) by 961 days.

(21) Appl. No.: 10/875,790

(22) Filed: Jun. 24, 2004

(65) Prior Publication Data

US 2005/0288765 A1 Dec. 29, 2005

(51) Int. Cl.
*A61F 2/06* (2006.01)
(52) U.S. Cl. .................................... 623/1.23
(58) Field of Classification Search ............... 623/1.11, 623/2.11
See application file for complete search history.

(56) References Cited

U.S. PATENT DOCUMENTS

| | | | |
|---|---|---|---|
| 5,617,878 A | 4/1997 | Taheri | |
| 5,800,521 A | 9/1998 | Orth | |
| 5,948,017 A * | 9/1999 | Taheri | 623/1.14 |
| 5,989,263 A | 11/1999 | Shmulewitz | |
| 6,030,414 A | 2/2000 | Taheri | |
| 6,099,548 A | 8/2000 | Taheri | |
| 6,102,938 A * | 8/2000 | Evans et al. | 623/1.35 |
| 6,106,549 A | 8/2000 | Taheri | |
| 6,253,768 B1 | 7/2001 | Wilk | |
| 6,409,750 B1 | 6/2002 | Hyodoh et al. | |
| 6,723,116 B2 | 4/2004 | Taheri | |
| 2002/0029077 A1 * | 3/2002 | Leopold et al. | 623/1.11 |
| 2005/0010277 A1 * | 1/2005 | Chuter | 623/1.13 |

OTHER PUBLICATIONS

Kato et al, Use of a Self-Expanding Vascular Occluder for Embolization During Endovascular Aortic Aneurysm Repair, 1997, Journal of Vascular and Interventional Radiology, vol. 8, Issue 1, p. 27-33 http://www.jvir.org/cgi/content/abstract/8/1/27.*

* cited by examiner

*Primary Examiner*—David Isabella
*Assistant Examiner*—Jonathan Stroud
(74) *Attorney, Agent, or Firm*—Walter W. Duft

(57) ABSTRACT

A system and method for exclusion of an aneurysm of an aortic arch region using a graft delivery system capable of maneuvering around an aortic arch, an aortic arch graft, and an occluder system for isolating an aneurysm while occluding one or more corresponding arteries, and with bypass of those arteries being performed using one or more selected bypass grafts. The graft may be branched or branchless. The graft delivery system has a flexible sheath that is manipulated manually with the aid of a guidance system. A hoist delivery system may also be provided. The occluder system may comprise independent occluders with one or more anchor members adjacent to one end. Alternatively, the occluders can be provided as part of the aortic arch graft, either as a built-in singular self-deploying occluder or as built-in multiple occluders. A kit is also provided containing a graft, stents, occluders, and optional delivery system.

18 Claims, 23 Drawing Sheets

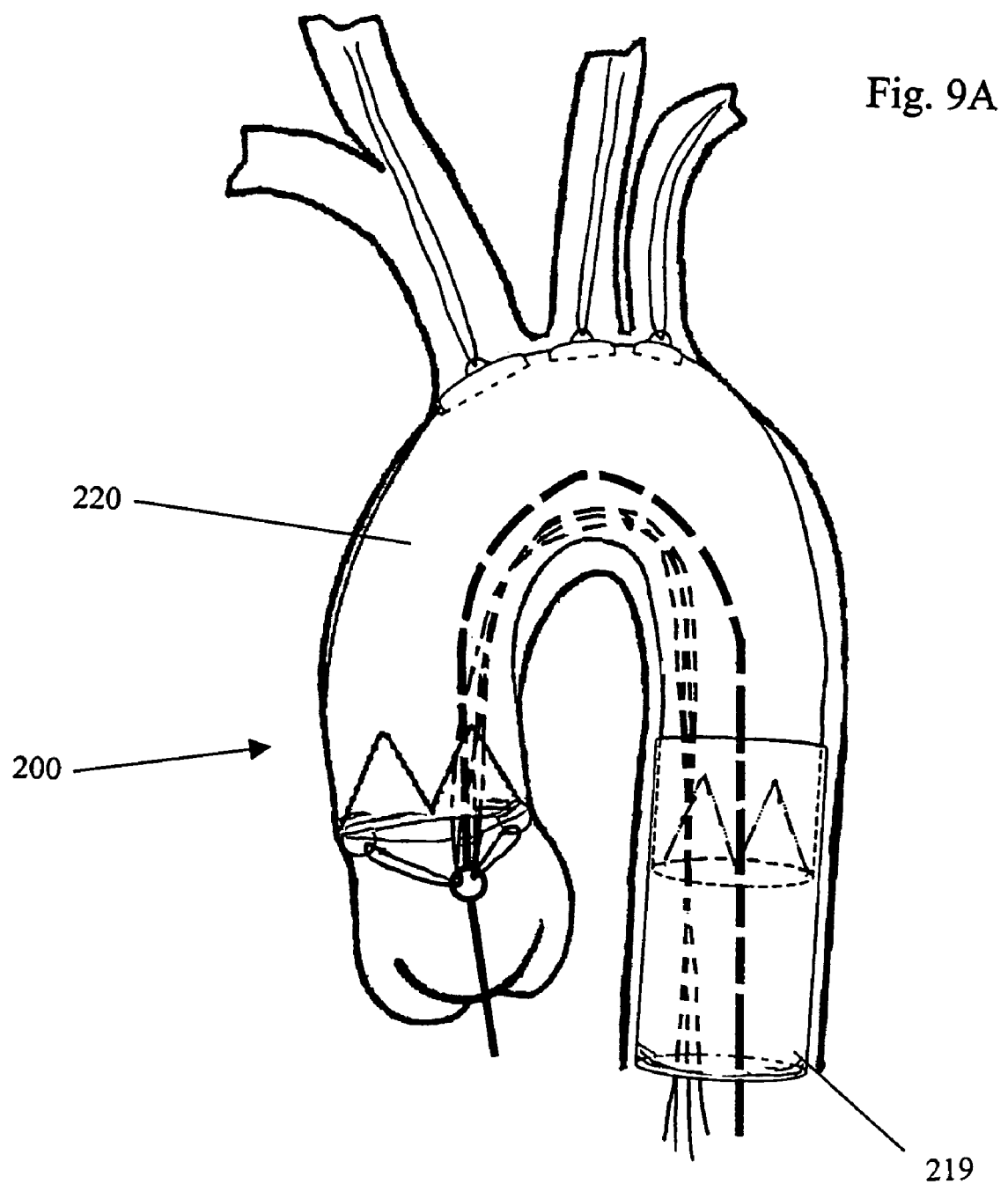

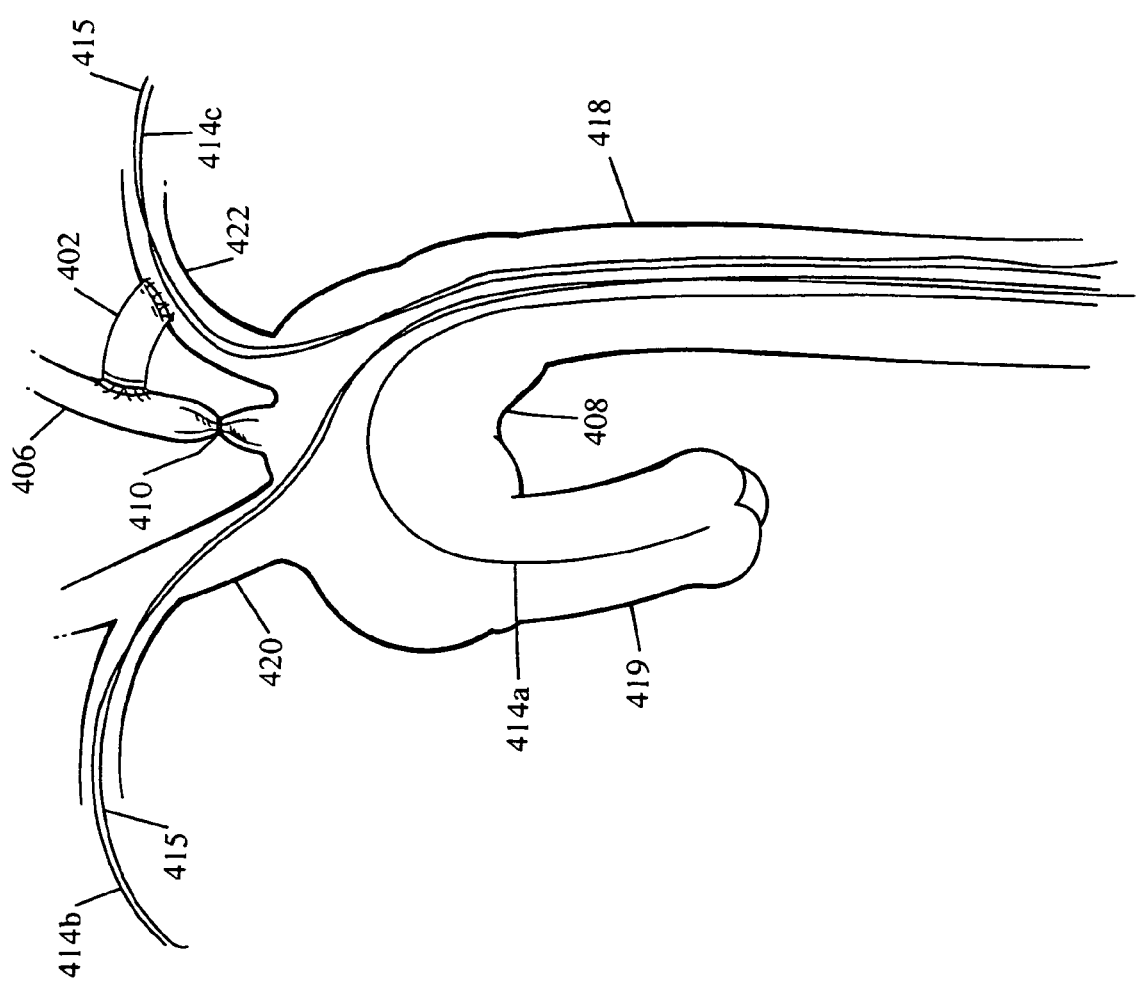

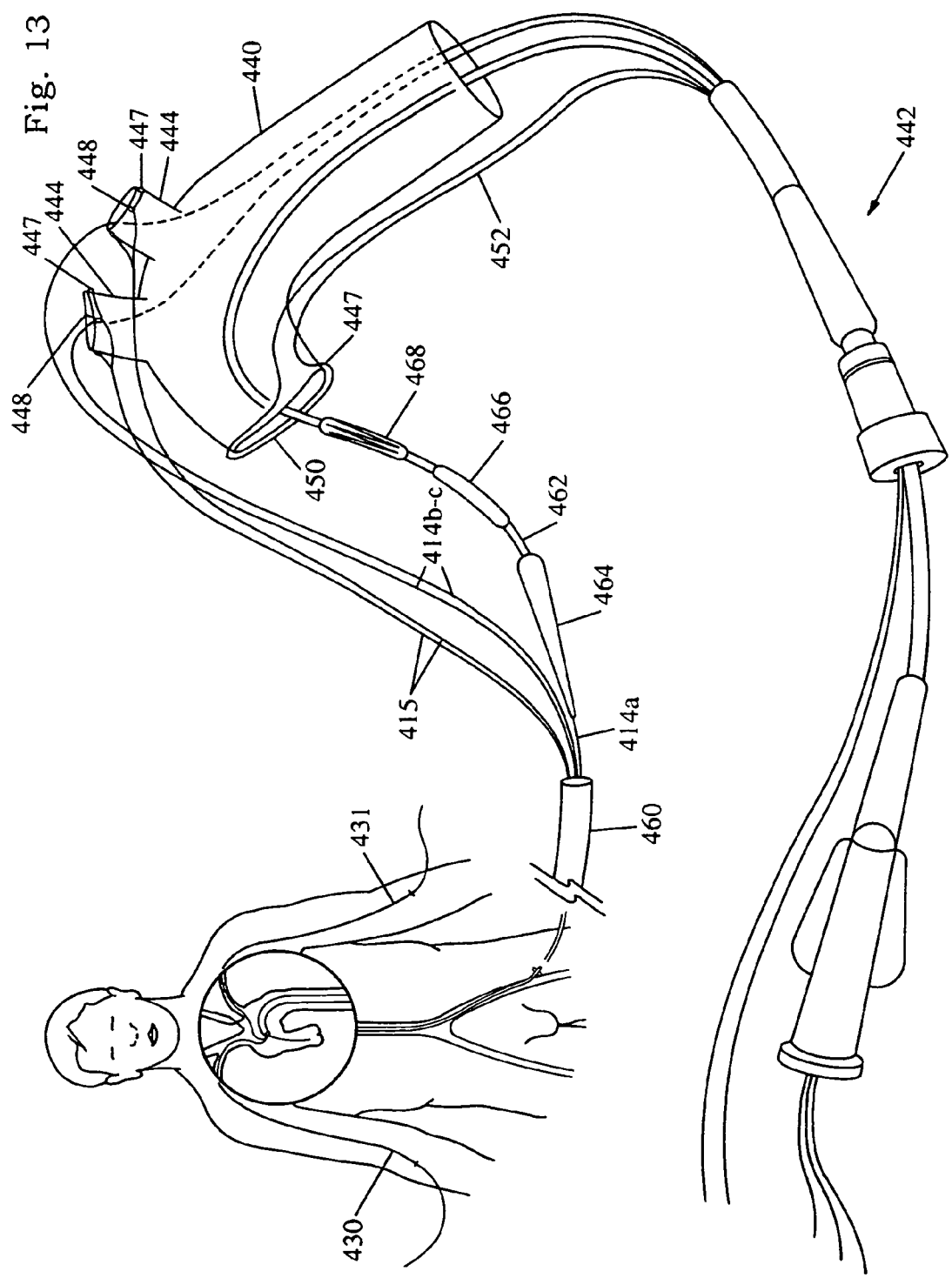

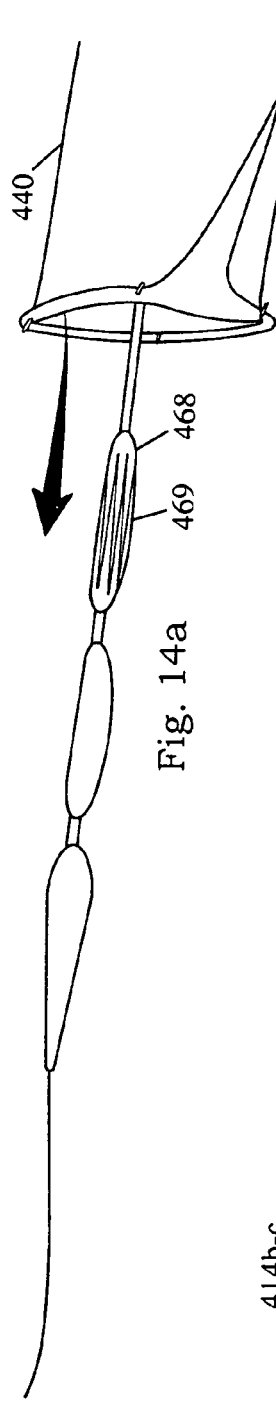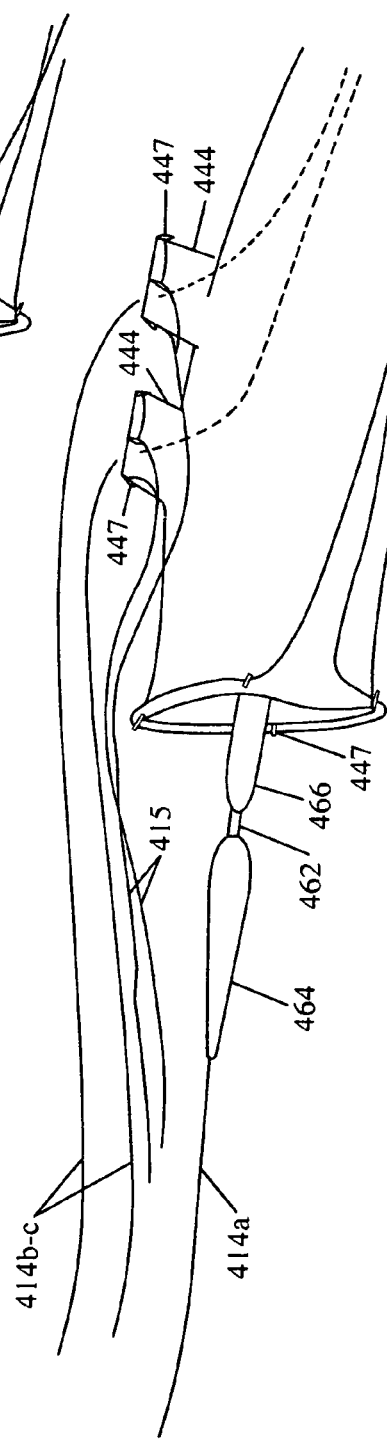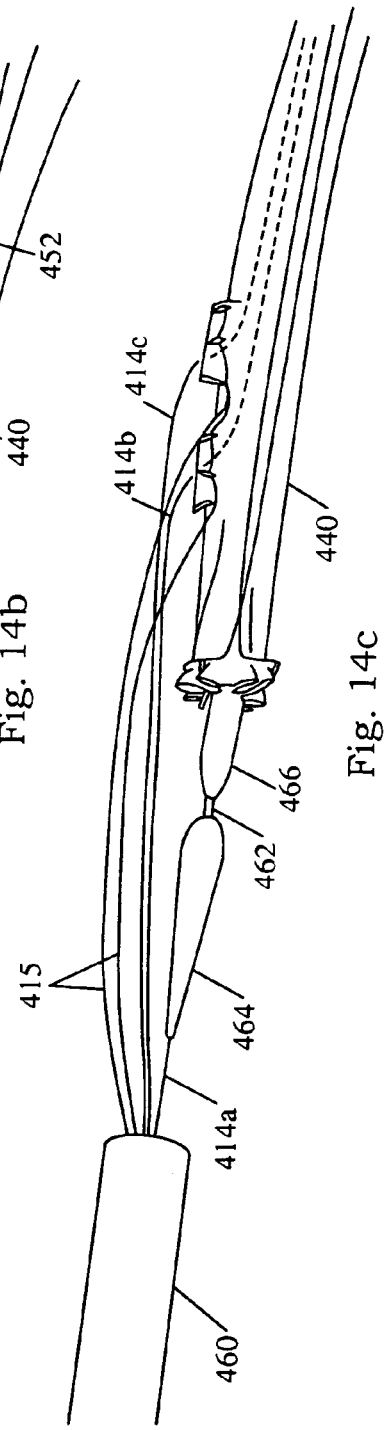

EXCLUSION OF ASCENDING/DESCENDING AORTA AND/OR AORTIC ARCH ANEURYSM

CROSS-REFERENCE TO RELATED APPLICATIONS

None

STATEMENT REGARDING FEDERALLY SPONSORED RESEARCH OR DEVELOPMENT

Not Applicable

BACKGROUND OF THE INVENTION

1. Field of the Invention

This invention relates to cardiovascular disease and the treatment thereof. More particularly, the invention pertains to a method and apparatus for treating an aneurysm of the ascending/descending aorta and/or aortic arch.

2. Description of the Prior Art

By way of background, existing techniques for exclusion of an aneurysm in the ascending/descending aorta and/or the aortic arch require the use of a heart lung machine and drastic reductions in patient body temperature, followed by excision and replacement of the diseased aortic arch section. These techniques are associated with a high rate of complications, morbidities, and mortalities. It would be desirable if an exclusion of an aortic arch region could be performed without entering the chest or mediastinum, as by use of a transfemoral or other percutaneous technique, and preferably requiring only local anesthesia and sedation.

SUMMARY OF THE INVENTION

The foregoing problems are solved and an advance in the art is obtained by a novel system and method for the exclusion of an aneurysm of the ascending/descending aorta and/or the aortic arch using an aortic arch graft and a graft delivery system capable of maneuvering around an aortic arch. An occluder system may also be provided for occluding one or more of the left subclavian artery, the left common carotid artery and the right innominate artery, and with bypass of one or more of those arteries being performed using selected bypass lumina.

In one embodiment of the invention, the aortic arch graft has branches and in another embodiment the aortic arch graft is branchless. The grafts may be stented or stentless, and they may have various additional features, such as connection members adapted for use during graft deployment, for stent restraint, for graft positioning or for other purposes.

In one implementation of a branchless aortic arch graft, the aortic graft has a built-in singular self-deploying occluder that provides the occluder system. The occluder is preferably sized to be larger than the distance in an aortic arch between a left subclavian artery and a right innominate artery. The occluder may contain an optional support ring sewn internally at the base of the occluder.

In another implementation of a branchless aortic arch graft, the graft has built-in multiple deployable occluders providing the occluder system. The occluders are preferably sized to respectively correspond to the diameters of a left subclavian artery, a left common carotid artery, and a right innominate artery. The occluders can be self-deploying or can be manually deployed by use of a guide member attached to the top of each occluder.

The graft delivery system of the invention may include a flexible tubular sheath surrounding a plunger mechanism, a catheter with a shaped tip, and a flexible guide wire. The sheath preferably has a flexible end that is capable of bending and maneuvering in any direction, up and around an artery or vessel. Manipulation of the flexible end can be performed with the aid of a guidance mechanism running end to end along the sheath. The guidance mechanism is adapted to be manipulated manually at the distal end of the sheath.

In an alternative implementation of the graft delivery system, a hoisting system is used to introduce the aortic arch graft. The graft has two or more connection members at one end, which can be attached with hoisting elements to an eyelet formed on the flexible guide wire. The hoisting elements and the guide wire extend internally through the graft. They are used to position the graft in an aortic arch and/or ascending/descending aorta by pulling on the hoisting elements after positioning the guide wire, and pulling the graft up towards the eyelet on the guide wire.

The occluder system of the invention may include individual occluders adapted to occlude one or more of a left subclavian artery, a left common carotid artery, and a right innominate artery. Each occluder may have one or more protruding anchor members adjacent to one end thereof. The anchor members are sized to anchor themselves to the wall of an artery.

The invention further contemplates an aortic arch aneurysm repair kit having an aortic arch graft, stents, occluders for occluding one or more of a left subclavian artery, a left common carotid artery, and a right innominate artery, and an optimal delivery system.

The invention further contemplates methods for repair of an ascending/descending aorta or aortic arch aneurysm. One method is for use with a branchless aortic arch graft. According to this method, a left carotid-subclavian bypass between the left common carotid artery and the left subclavian artery is performed, together with a bilateral femoral-axillary bypass between the right femoral artery and the right subclavian artery, and between the left femoral artery and the left subclavian artery. Next, the left subclavian artery, the left common carotid artery, and the right innominate artery are occluded proximate to the aortic arch. A branchless aortic arch graft is then introduced via a percutaneous approach and positioned in the ascending/descending aorta and/or aortic arch. Another method in accordance with the invention is for use with a branched aortic arch graft. According to this method, a left carotid-subclavian bypass between the left common carotid artery and the left subclavian artery is performed. Next, the left carotid artery is occluded proximate to the aortic arch. A branched aortic arch graft is then introduced via a percutaneous approach and positioned in the ascending/descending aorta and/or aortic arch and respective branches.

BRIEF DESCRIPTION OF THE DRAWINGS

The foregoing and other features and advantages of the invention will be apparent from the following more particular description of preferred embodiments of the invention, as illustrated in the accompanying Drawings, in which:

FIGS. 4a and 4b are cross sectional centerline views of the proximal end of a graft delivery system in accordance with the present invention in which FIG. 4a and 4b show alternative constructions of a sheath introducer;

FIGS. 9a and 9b are perspective views showing deployment of a modified version of the graft of FIG. 3a using the delivery system of FIG. 8a;

FIG. 12 is a diagrammatic view showing an aortic arch, and further illustrating a left carotid brachial bypass lumen.

FIG. 13 is a perspective view of a branched aortic arch graft of the present invention, and a graft delivery system in accordance with the present invention.

FIGS. 14a, 14b, and 14c are perspective views of the graft of FIG. 13 being prepared for introduction into the delivery system of FIG. 13.

DETAILED DESCRIPTION OF THE PREFERRED EMBODIMENT

A. Introduction

Figure 1:
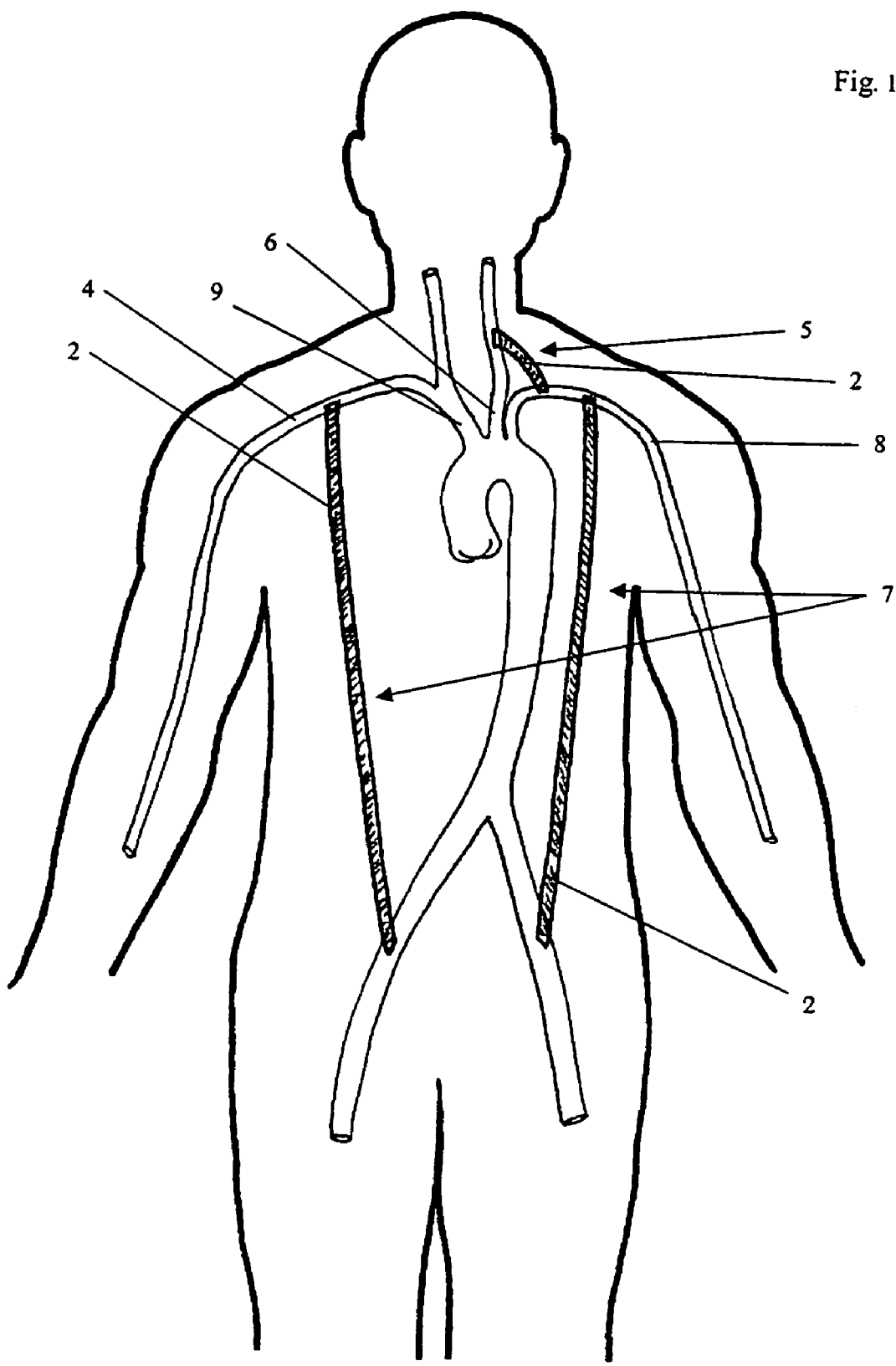
FIG. 1 is a diagrammatic view showing an outline of the human body and a portion of the circulatory system, and further illustrating a left carotid-subclavian bypass, a right femoral-axillary bypass, and a left femoral-axillary bypass.

The system and method of the invention will now be described by way of exemplary embodiments shown by the drawing figures, in which like reference numerals indicate like elements in all of the several views. The terms distal and proximal are used herein and will be understood to indicate position relevant to the heart, with proximal indicating a position closer to the heart and distal indicating a position farther away from the heart.

As summarized above, the invention represents a departure from the conventional techniques for repairing an aneurysm of the aortic arch or ascending/descending aorta in which the diseased section is excised and replaced. The invention contemplates the insertion of the aortic arch graft to isolate the diseased section from blood flow. This presents a challenge because the aortic arch has three branches connected to the left subclavian artery, left common carotid artery and a right innominate artery. The present invention proposes two solutions, one being the use of an aortic arch graft with branches and the other being the use of a branchless aortic arch graft with occlusion of the aortic branches.

B. Branchless Aortic Arch Graft

As indicated, one solution to the aortic arch repair challenge is to implant a branchless aortic arch graft without cutting off blood supply to the arteries leading from the aortic branches. This is can be done by performing an arterial bypass procedure prior to graft introduction, as shown in FIG. 1. First and second surgical teams using arterial bypass grafts 2 can implement the bypass procedure. The bypass grafts are conventional in design and material and may be of the same type used for femoral-axillary bypass procedures. A first surgical team performs a left carotid-subclavian bypass 5, in which a bypass graft 2 is placed between the left carotid artery 6 and the left subclavian artery 8. A second surgical team performs a bilateral femoral-axillary bypass 7 in which bypass grafts 2 are respectively placed between the right subclavian artery 4 and the right femoral artery and between the left subclavian artery 8 and the left femoral artery. The left common carotid artery 6, left subclavian artery 8, and right innominate artery 9 may then be occluded proximate to an aortic arch either prior to or part of the graft deployment procedure.

Figure 2A:
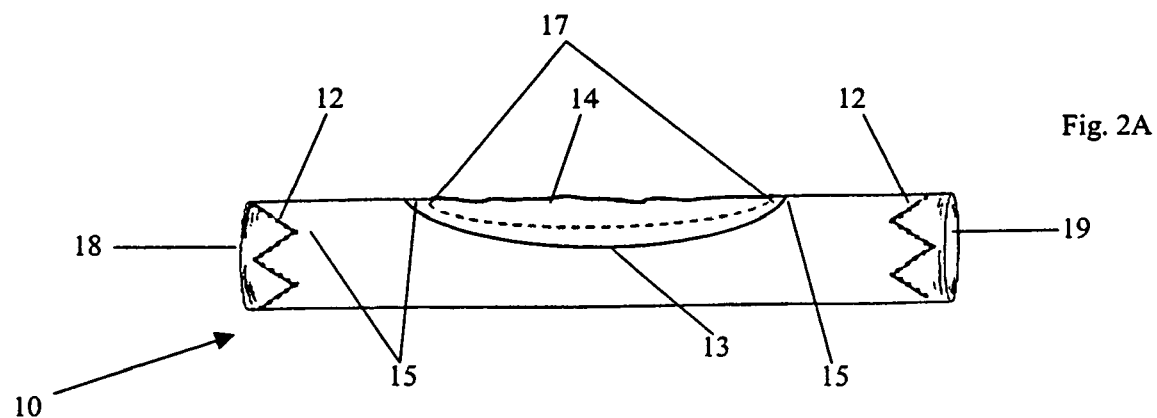
FIG. 2a is a side view of a branchless aortic arch graft of the present invention with a built-in self-deploying occluder in a non-deployed condition.
Figure 2B:
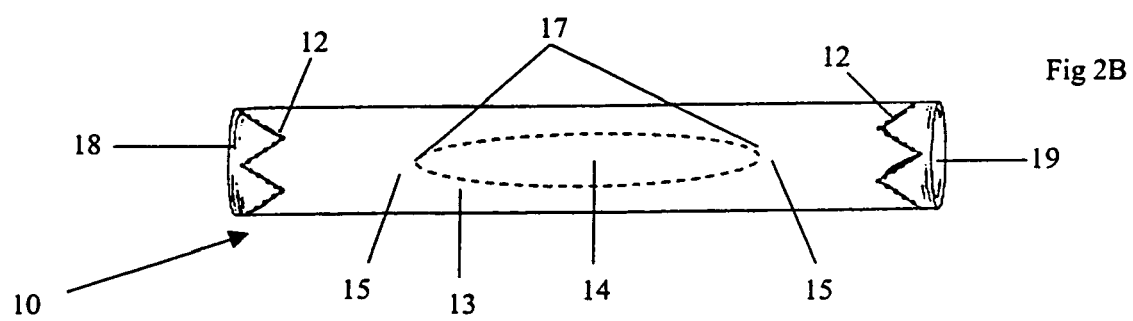
FIG. 2b is a top view of the graft of FIG. 2a in a non-deployed condition.

Following the bypass procedure, an aortic arch graft can be deployed in the aortic arch and/or ascending aorta to exclude the aneurysm, followed by occlusion of the branches of the aortic arch. FIGS. 2a and 2b show an exemplary branchless aortic arch graft 10 that may be used for this purpose. The graft 10, which can be constructed of dacron or other suitable biocompatible material, has a tubular shape when in its expanded state and is capable of being folded or twisted for loading into a sheath introducer (See FIGS. 4a and 4b). The graft 10 has a first open end 18 and second open end 19. Each end may have a stent 12 mounted thereto by sewing or the like. Alternatively, stents may be inserted following graft deployment. The graft 10 further includes a single self-deploying occluder 14. The occluder 14 is preferably made from additional graft material that is sewn or otherwise attached to the wall of the graft 10. Sufficient material is used so that the occluder 14 is capable of deploying laterally outward beyond the nominal tubular shape of the graft 10. The occluder 14 is preferably elliptical in shape, but other shapes could be used. It extends along the partial length of the graft 10 and is preferably sized to be larger than the distance in an aortic arch between a left subclavian artery and a right innominate artery.

An opening is formed in the wall of the graft 10 that allows blood to flow into the occluder 14 from the main body of the graft (see below). A support ring 13 may be provided at a base 17 of the occluder 14 to help define the opening. The support ring 13 can be made of nitonol and is preferably 1-2 mm larger than the base 17 of the occluder 14. As described in more detail below relative to FIG. 6, the graft 10 can be positioned by using one or more iodinated radio-opaque markers 15.

Figure 2C:
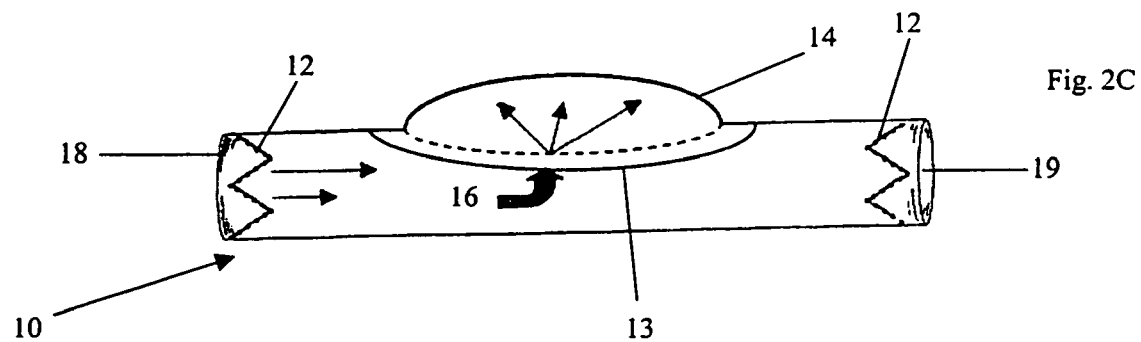
FIG. 2c is a side view of the graft of FIG. 2a in a deployed condition.

In FIG. 2c, the occluder 14 of the graft 10 is seen from a side view in a deployed state. Deployment occurs as blood flow 16 forces the wall of the occluder 14 to move laterally beyond the girth of the graft 10.

The stents 12 can be formed as conventional spring stent members made from a shape memory material such as nitonol (nickel-titanium alloy) that self deploy upon insertion. Alternatively, they may be formed as non-self deploying stents. In either case, the stents 12 must be sized for use in the ascending/descending aorta or aortic arch. Note that only two stents are desirable because of the curved shape of the aortic arch.

Figure 3A:
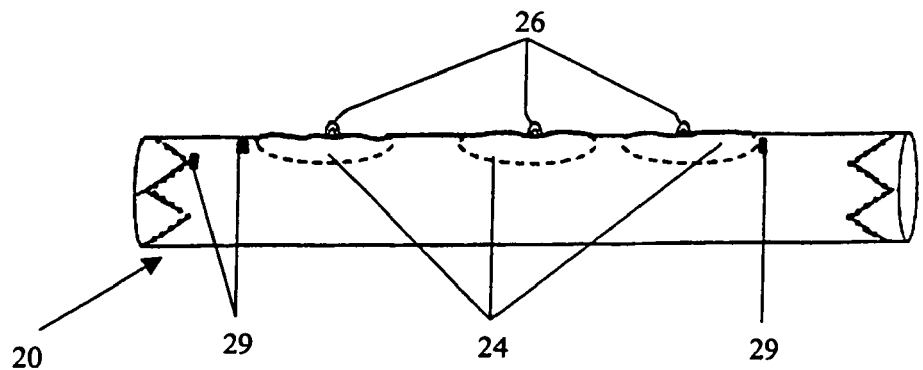
FIG. 3a is a side view of an alternate branchless aortic arch graft of the present invention with multiple built-in occluders.
Figure 3B:
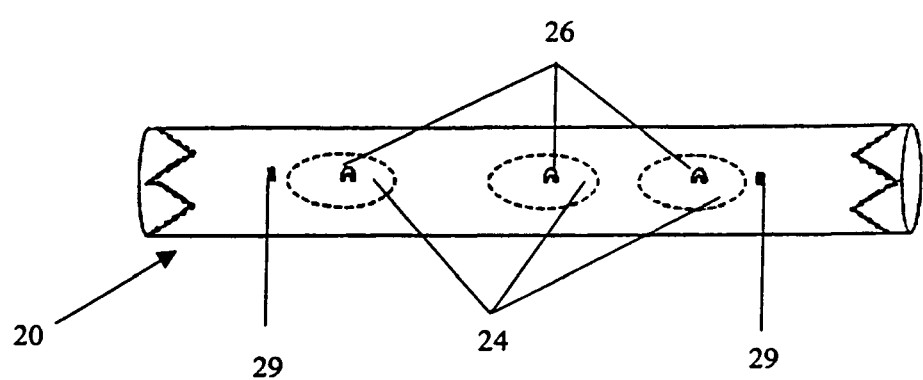
FIG. 3b is a top view of the graft of FIG. 3a in a non-deployed condition.
Figure 3C:
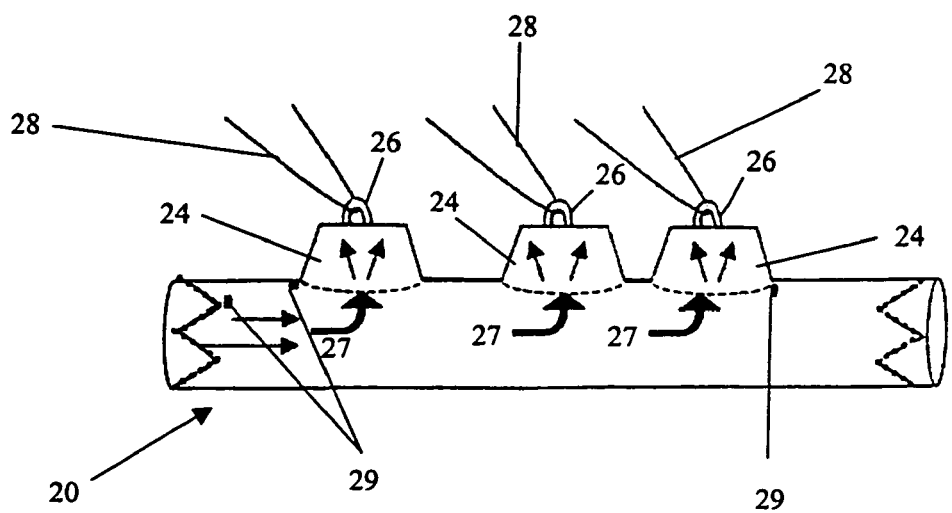
FIG. 3c is a side view of the graft of FIG. 3a in a deployed condition.

Turning to FIGS. 3a and 3b, another embodiment of an aortic arch graft 20 is similar in construction to the graft 10, but is provided with multiple occluders 24 instead of a single occluder. The occluders 24 may include loop members 26 located externally at the end of each occluder 24. The loop members 26 may be closed or partially open such that strings/filaments or other occluder deployment members 28 may be threaded or otherwise attached for manual deployment of the occluders 24. FIG. 3c shows a side view of the graft 20 with the occluders 24 in a deployed state. By way of example only, the strings 28 can be threaded through loop members 26 and pulled to expand the occluders 24 from the main body of the graft 20. In an alternative construction, the occluders 24 can be adapted to be self-deployable by virtue of blood flow 27. As described in more detail below in FIG. 6, the graft 20 is positioned using iodinated radio-opaque markers 29.

Figure 4A:
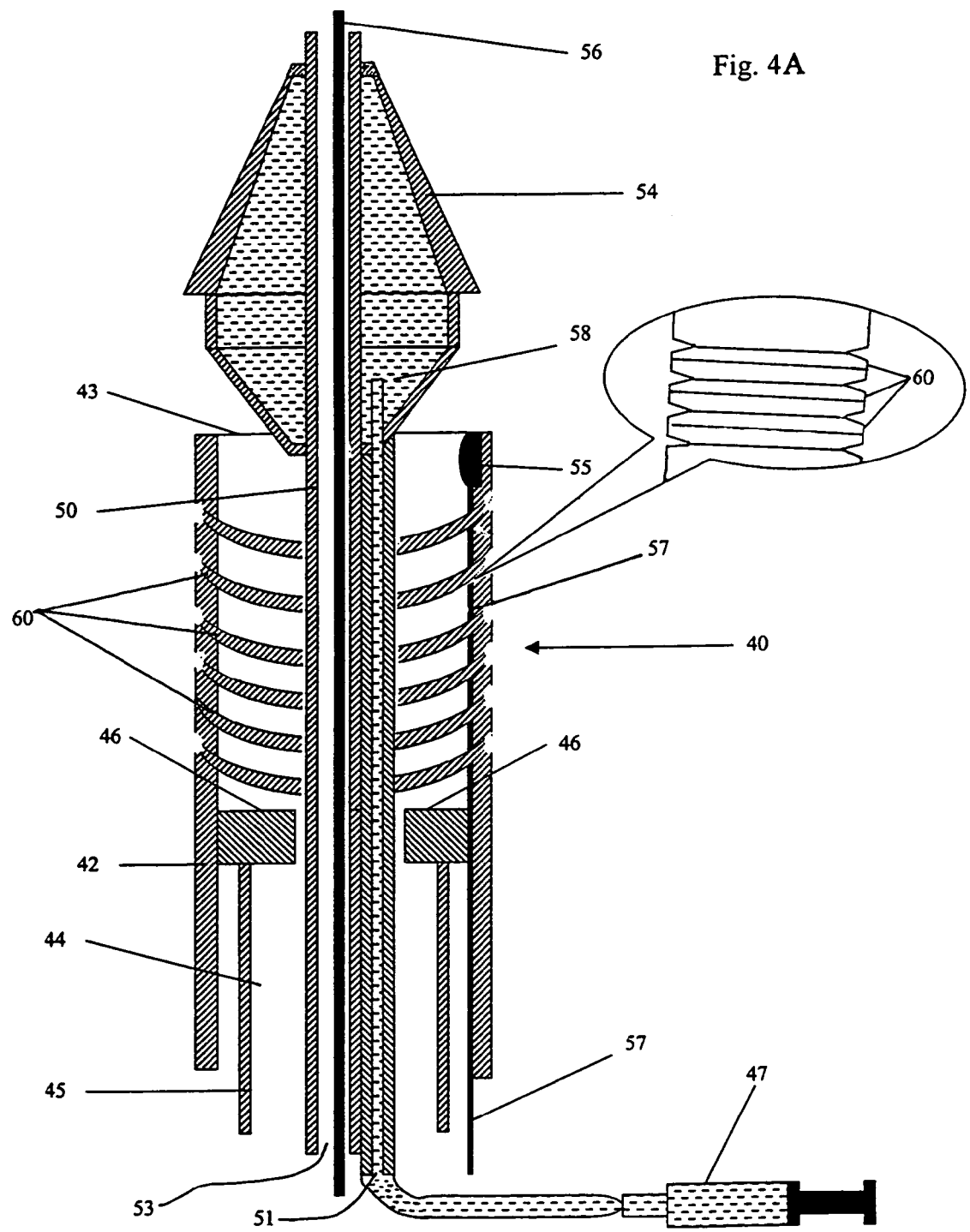

Turning now to FIG. 4a, a delivery system 40 for positioning any of the aortic graft assemblies herein includes a sheath introducer 42 surrounding a plunger assembly 45, which itself surrounds a catheter 50. The sheath introducer 42, which can be made from biocompatible plastic or any other biocompatible, substantially flexible material, is a generally tubular member with a proximal end 43 and distal end (not shown), each end being provided with an opening. To provide the flexibility required to negotiate the aortic arch, the sheath 42 can be constructed with flexible ribs 60 running from the proximal end 43 down the shaft of the sheath introducer about one to three inches. By way of example only, the flexible ribs 60 can be configured as shown in the inset of FIG. 4a. The plunger assembly 45 is of standard construction. It includes a central lumen 44 for passage over the catheter 50, and a plunger head 46 located at the most proximal part of the plunger assembly. The plunger head 46 preferably has a substantially flat proximal surface for contacting a graft assembly as described herein so that the plunger assembly 45 is able to push the graft in a proximal direction relative to the sheath introducer 42 during graft deployment. The catheter 50 is substantially tubular with two hollow interior passages 51 and 53. A proximal end of the catheter 50 is equipped with a hydraulic inflatable tip 54 that is adapted to be filled with a liquid 58, preferably saline. A suitable injection device, such as an attachable syringe 47, is used to force solution up through the hydraulic passage 51 of the catheter 50 and into the catheter tip 54. The catheter passage 53 is conventionally adapted to receive a guide wire 56 to direct the delivery system 40 through appropriate arteries as part of a transfemoral approach.

An optional internal guidance mechanism 55 can be provided to enable the proximal end 43 of the sheath 42 to bend and maneuver multi-directionally, up and around an artery or vessel. The guidance mechanism 55 can be implemented in a variety of ways, but is shown by way of example only in FIG. 4a as including a wire/filament 57 attached to the proximal end 43 of the sheath 42. The wire/filament 57 runs end to end along the inside of the sheath 42, and is activated manually at the distal end thereof. If desired, a suitable control device, such as a knob or lever (not shown) could be attached to allow manipulation of the wire/filament 57.

Figure 4B:
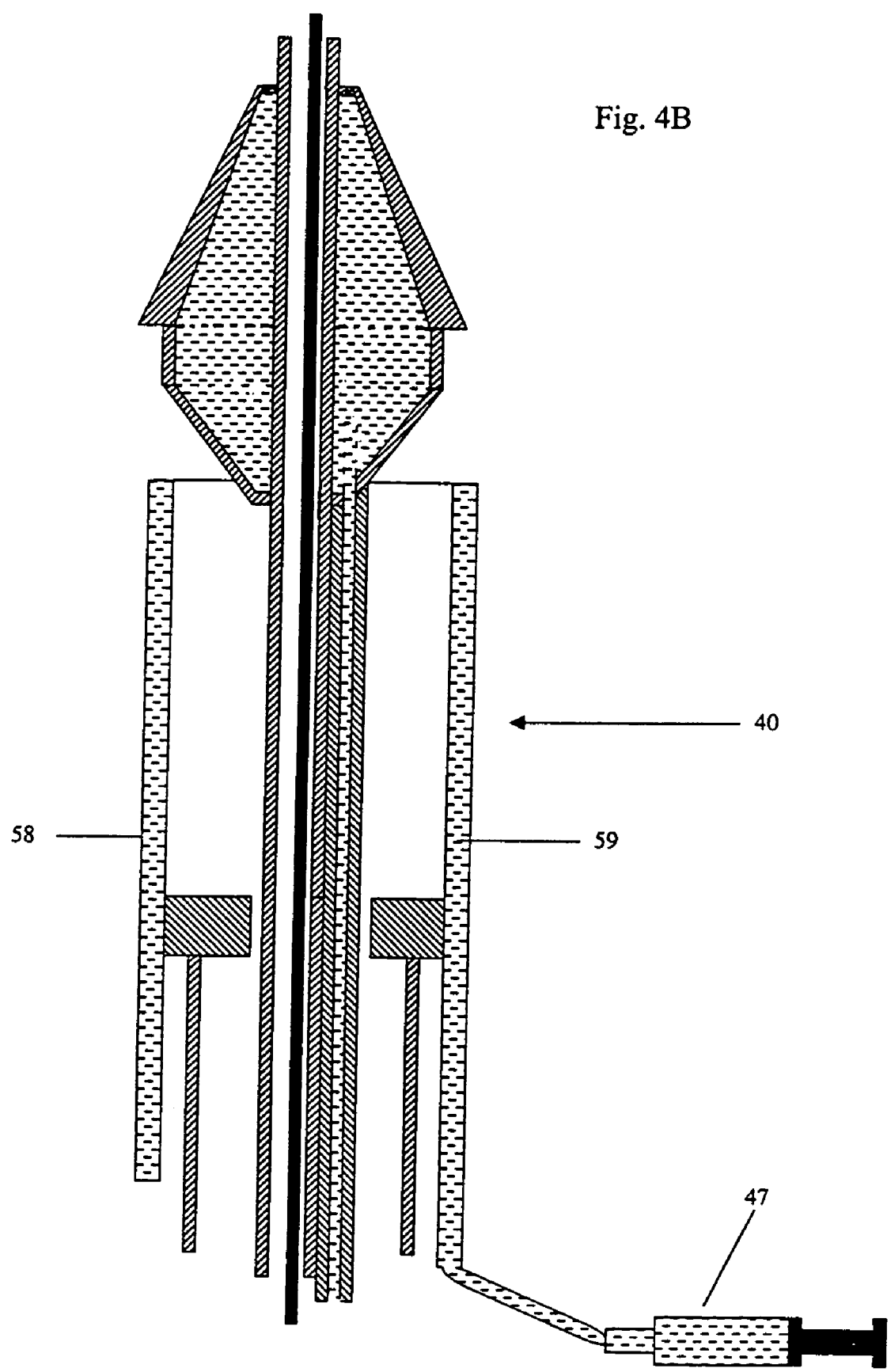

FIG. 4b illustrates an alternative way in which a sheath introducer can be constructed with the required flexibility to allow its use in the delivery system 10. In particular, a sheath introducer 58 is formed with a hollow wall 59 that is adapted to be filled with a liquid, preferably saline, to provide various states of rigidity by controlling the hydraulic pressure within the wall 59. A suitable injection device, such as an attachable syringe 47, is used to force solution up through the wall 59 of the sheath introducer 58 until the sheath introducer 58 is of a desired rigidity. Note that all other structure shown in FIG. 4b is identical to that shown in FIG. 4a, and its description will not be repeated.

Figure 5:
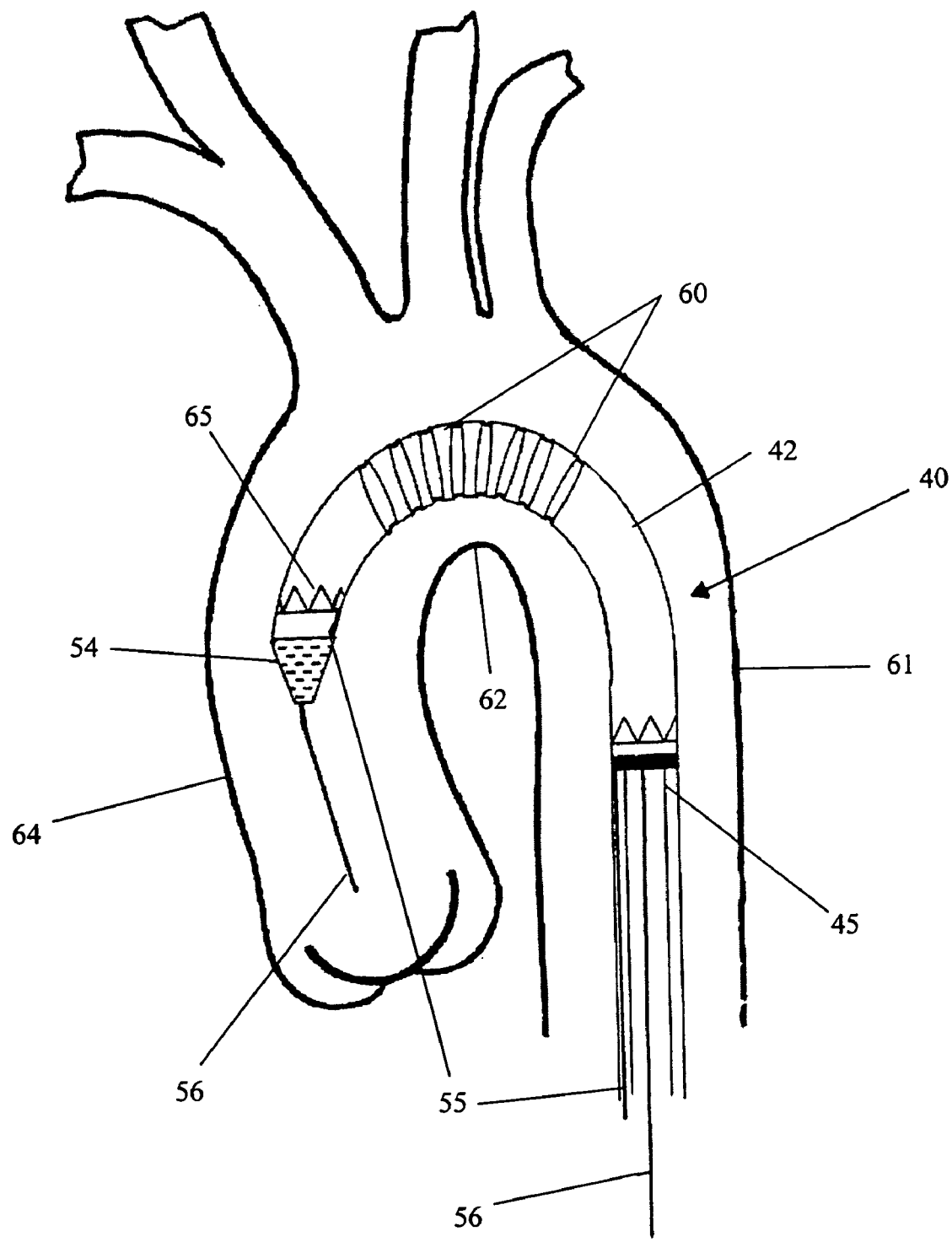
FIG. 5 is a perspective view showing the delivery system of FIG. 4a deployed within an aortic arch and advancing into an ascending aorta.

The delivery system 40 can be used to deploy an aortic arch graft (such as the grafts 20 and 40) according to the following procedure: After opening a femoral artery (right or left), the guide wire 56 is inserted therein and passed through the descending aorta, around the aortic arch, through the ascending aorta, and into the aortic valve of the heart. Note that the guide wire 56 has a relatively blunt tip so that it does not damage any blood vessel walls. Next, the proximal end of the catheter 50 of the delivery system 40 is inserted over the distal end of the guide wire 56. The delivery system 40 will have been previously loaded with an aortic arch graft inside of the sheath introducer 42. After inflating the catheter tip 54 with the liquid to a desired pressure, the delivery system 40 is inserted into the femoral artery and passed through the descending aorta 61, the aortic arch 62, and into the ascending aorta 64 as depicted in FIG. 5. As the catheter tip 54 reaches the aortic arch 62, the guidance mechanism 55 (if present) is used to bend the sheath introducer 42 (or 58) to direct the delivery system 40 to the ascending aorta 64, where it is positioned using iodinated radio-opaque markers on graft. With the delivery system 40 in position, the graft 65 is deployed from the sheath introducer 42 (or 58) using the plunger 45. With the proximal end of the graft sufficiently secured to the vessel wall by virtue of its proximal stent, the sheath introducer 42 (or 58) is withdrawn from the ascending aorta 64 and the descending aorta 61 as the plunger 45 simultaneously deploys the remaining length of the graft around the aortic arch 62 and down to the descending aorta 61. With the distal end of the graft sufficiently secured in position by virtue of its distal stent, the catheter tip 54 is deflated and pulled through the interior of the graft until it reaches the proximal end of the sheath introducer 42 (or 58). The delivery system 40 is then removed from the body, followed by the removal of the guide wire 56.

Figure 6:
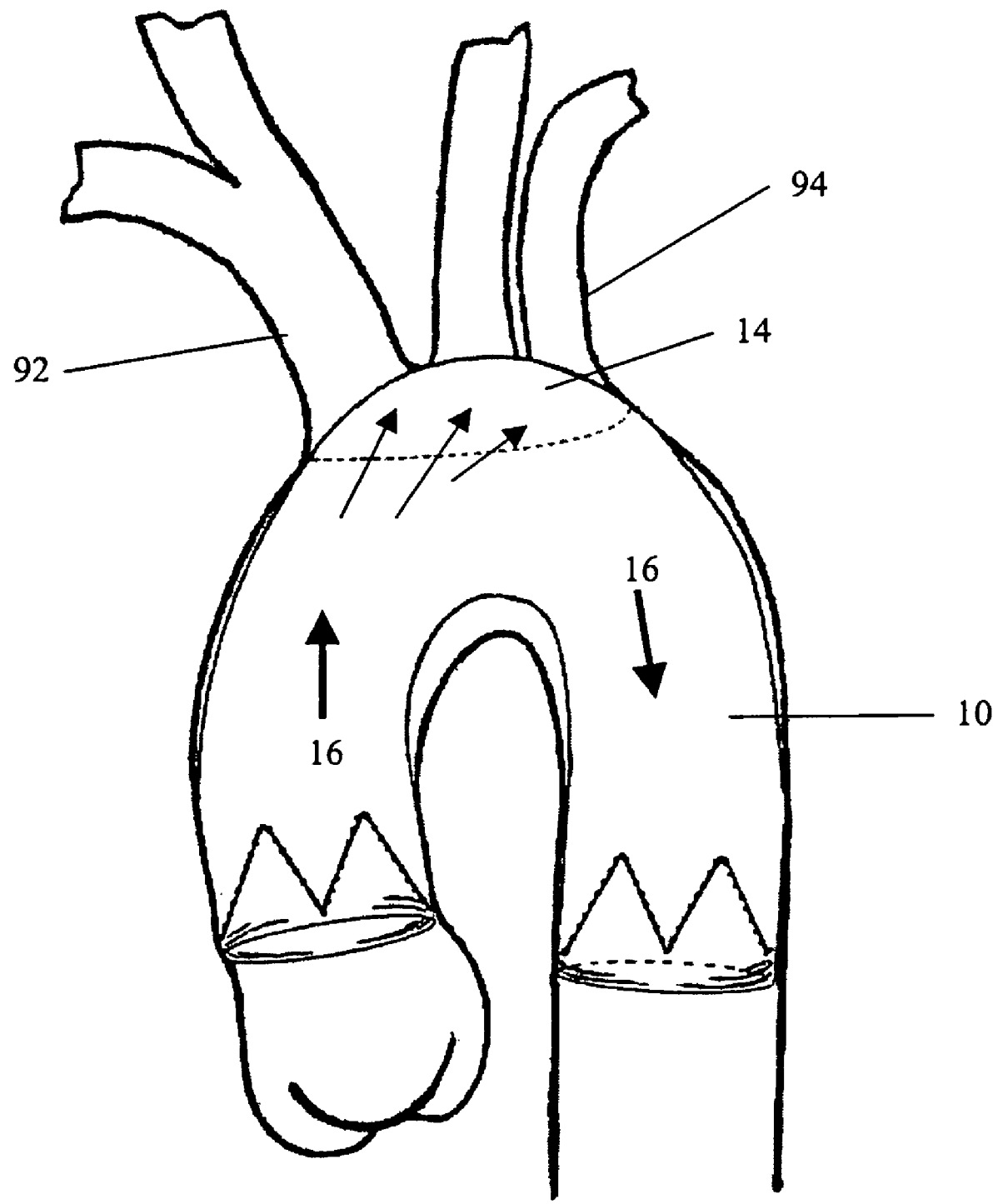
FIG. 6 is a perspective view of the branchless graft of FIG. 2a showing the graft deployed in an aortic arch.

If the delivery system 40 is used to implant the aortic arch graft 10 of FIG. 2a, the implantation procedure described above will result in the graft 10 being deployed in the aortic arch in the manner shown in FIG. 6. As blood flows through the graft 10, (shown at 16) the wall of the single occluder 14 will be forced laterally outward by the force of the blood flow 16 at least the distance between the right innominate artery 92 and left subclavian artery 94. Due to pressure differential, this force will be greater than the force asserted from blood flow within the occluded arteries. The occluder 14 will thus be retained in position.

Figure 7A:
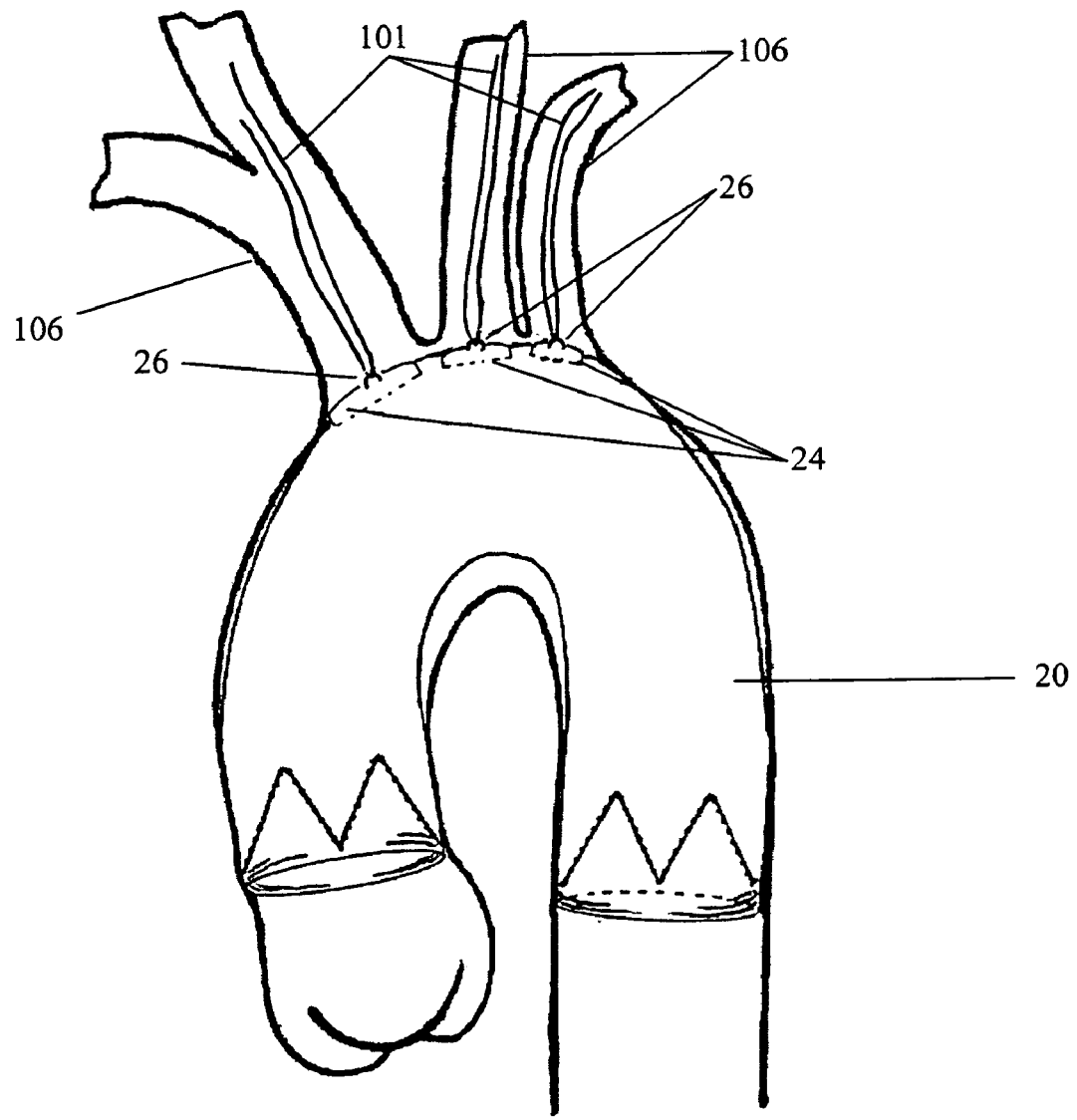
FIG. 7a is a perspective view of the branchless graft of FIG. 3a showing the graft deployed in an aortic arch, but prior to deployment of occluders.
Figure 7B:
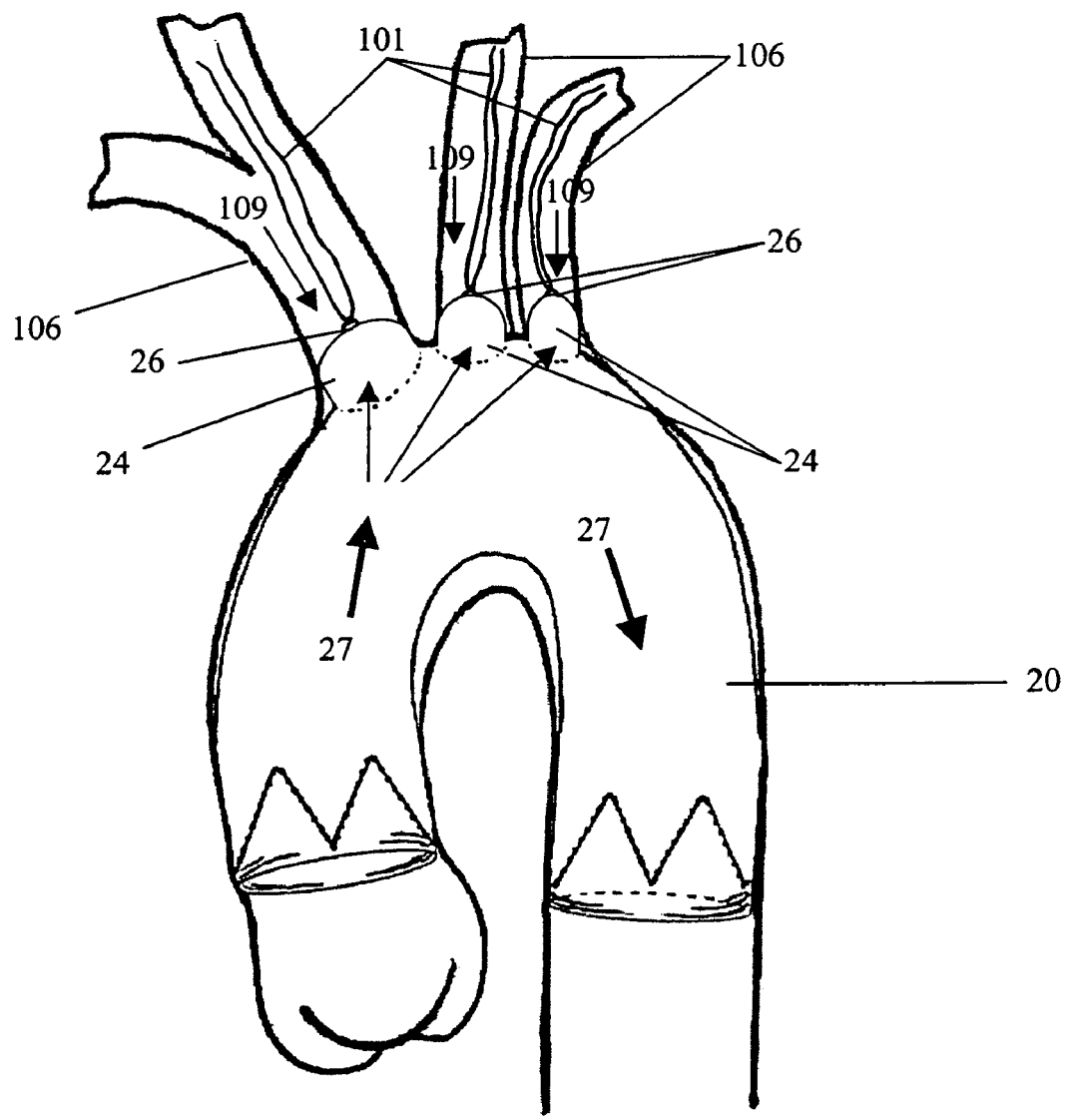
FIG. 7b is a perspective view of graft of FIG. 3a with occluders being deployed using strings in the branches of an aortic arch.

If the delivery system 40 is used to implant the aortic arch graft 20 of FIG. 3a, the implantation procedure described above will result in the graft 10 being deployed in the aortic arch in the manner shown in FIGS. 7a and 7b. Although the graft 20 is introduced in the manner described above relative to FIG. 5, delivery of this type of graft includes the additional step of temporarily attaching occluder deployment members, such as strings/filaments 101, to the occluders 24 before the graft 20 is loaded into the sheath introducer 42 (or 58). The strings/filaments 101 can be respectively inserted into the right innominate artery, left carotid artery, and left subclavian artery and pulled from their point of entry, passed through the descending aorta, into the femoral artery, and out of the vessel at the groin. Next, the strings/filaments 101 are temporarily attached to the loop members 26 of the corresponding occluders 24 of the graft 20. The graft 20 is then loaded into the sheath introducer 42 (or 58). As the delivery system 40 is inserted into the femoral artery and advanced for positioning in the aortic arch 64, the strings/filaments 101 are simultaneously pulled, remaining relatively taut and forward of the delivery system 40 to prevent entanglement within the arterial vessels. FIG. 7a shows the graft 20 in position and ready for the occluders 24 to be deployed by way of a final pulling of the strings/filaments 101 temporarily attached to the loop members 26. One at a time (or simultaneously), the attached strings/filaments 101 are pulled to assist movement of the occluders 24 up into a corresponding artery 106, blocking blood flow and occluding the artery as seen in FIG. 7b. Because the force of the blood flow 27 within the graft 20 is greater than the force being asserted from blood flow 109 within the occluded arteries 106 the occluders 24 will remain in a deployed state. After the occluders 24 are sufficiently secured, the strings/filaments 101 are detached from the loop members 26 of the occluders 24 by pulling one end until the opposing end is fully withdrawn from the body. Although not shown, a modified version of the graft 20 wherein the occluders 24 do not have loop members 26 and are not deployed with strings/filaments 101 could also be used. In this instance, the occluders 24 would be deployed by the blood flow 27 alone, which forces the occluders 24 to expand out from the graft 20 and into position in the arteries 106, which are thereby occluded. The occluders 24 will then remain in a deployed state due to blood flow pressure differential, as described above. Alternatively, each occluder 24 could be stabilized with a stent (not shown).

Figure 8A:
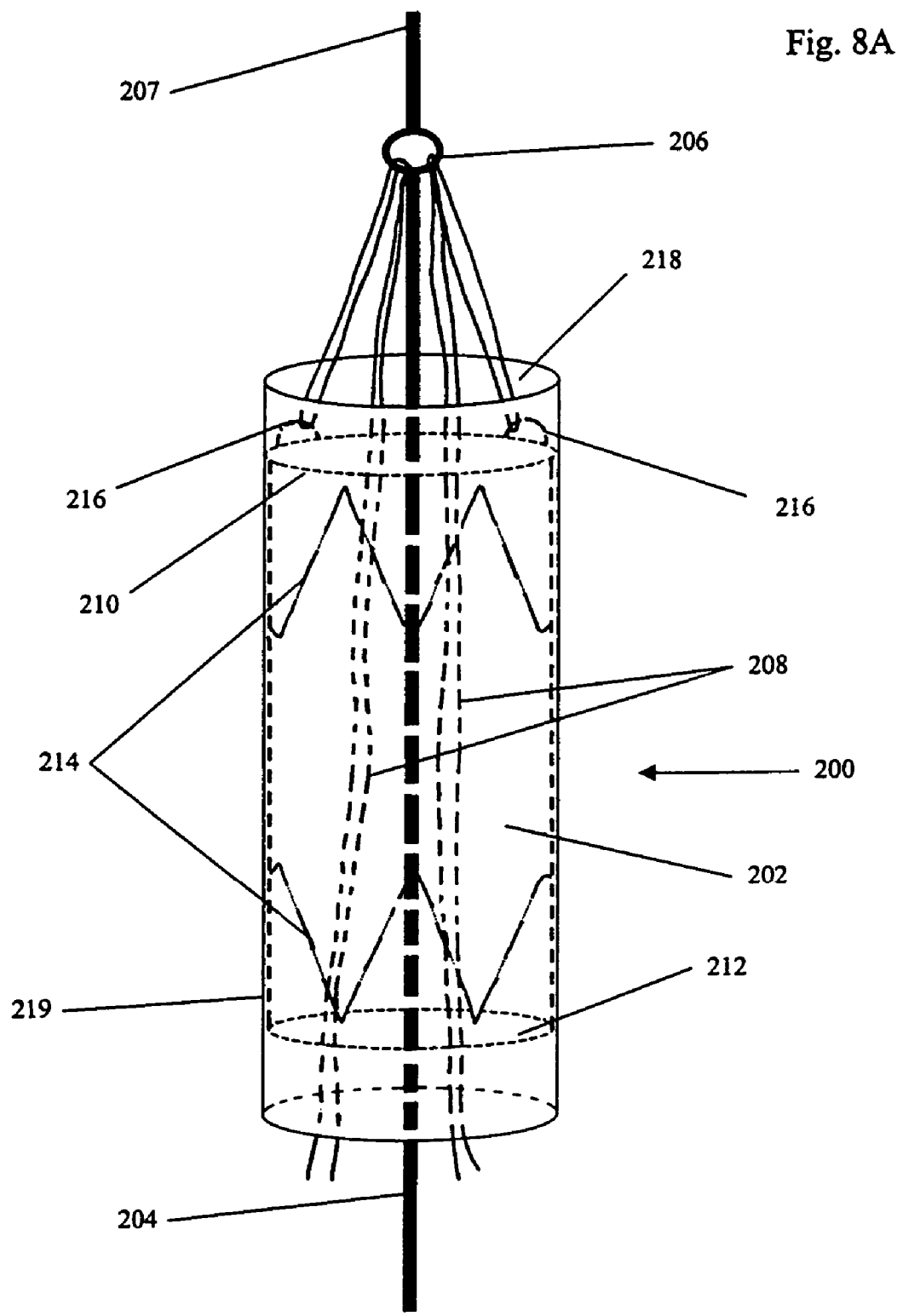
FIGS. 8a and 8b are perspective views of an alternate delivery system of the present invention for use with a branched or branchless aortic arch graft with multiple loop connection members at its proximal end, and with the graft being stented and FIGS. 8a and 8b respectively showing alternative methods for compressing the stents during graft introduction.
Figure 8B:
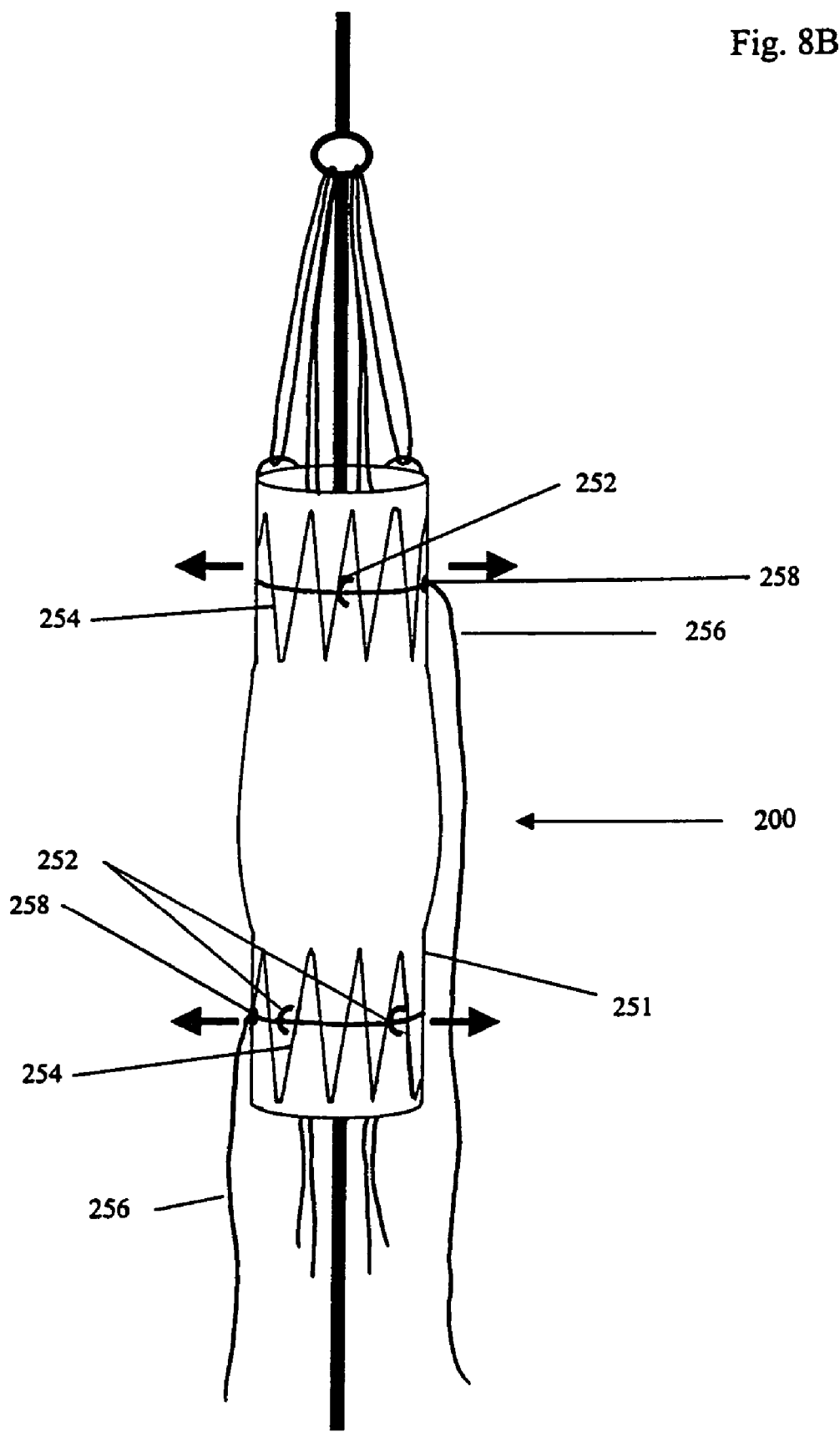
Figure 9B:
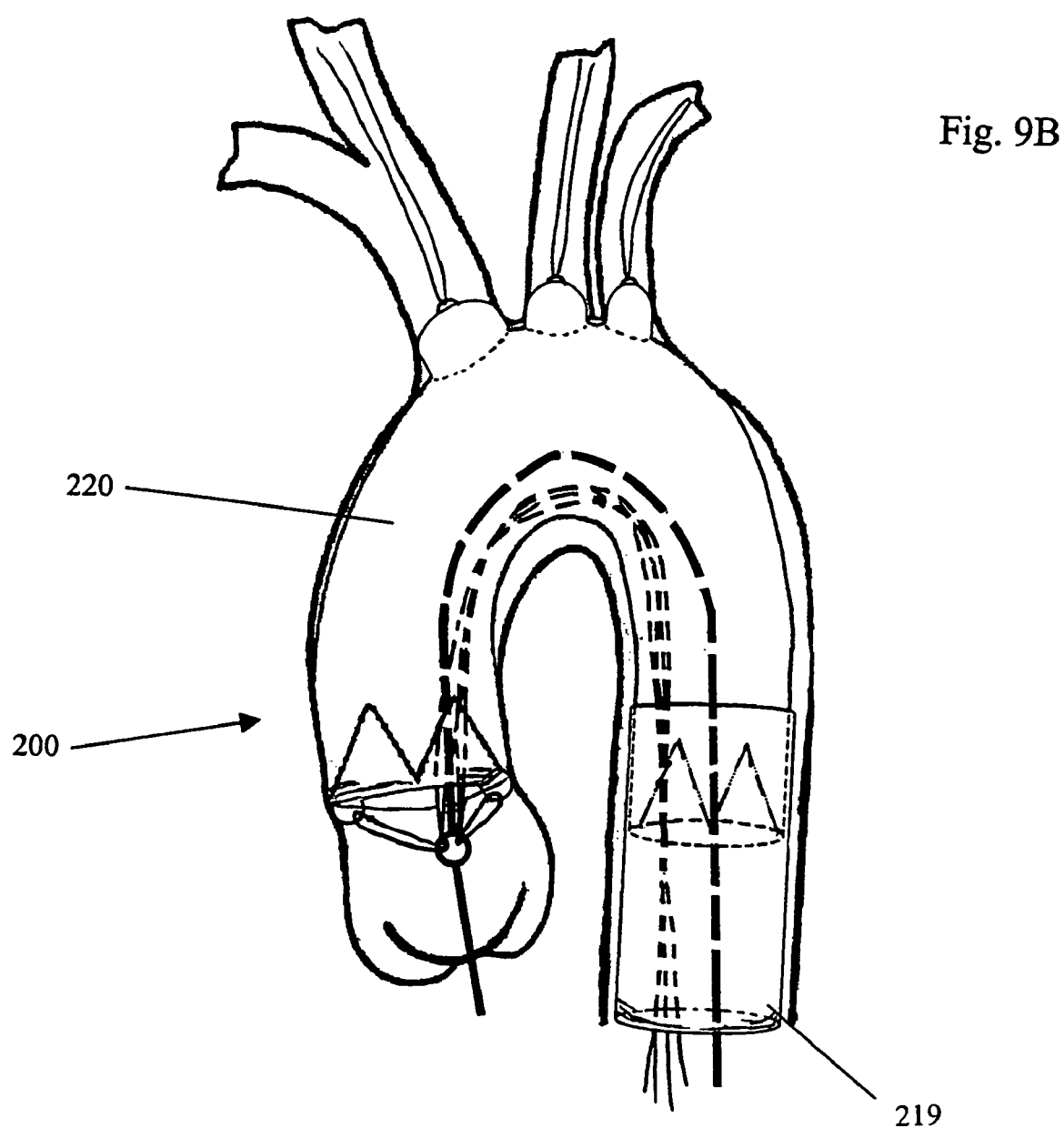

Turning now to FIGS. 8a and 8b, an alternate delivery system 200 featuring a graft hoisting arrangement can be used to position an aortic arch graft 202 in an ascending/descending aorta and/or an aortic arch. The delivery system 200 includes a flexible guide wire or catheter 204, made of plastic or other suitable material, with an eyelet 206 at or near its proximal end 207 (which is preferably blunt tipped), and hoisting elements, such as strings 208. The graft 202 includes a first open proximal end 210 and second open distal end 212, each end having a stent 214 mounted thereto by sewing or the like. Alternatively, stents may be inserted following graft deployment. The graft 202 can be constructed with one or more occluders, as shown in FIGS. 9a and 9b, which depict the graft 202 in a deployed position. With or without occluders, the graft 202 is constructed with two or more loop members 216 (or other suitable attachment elements) at the proximal end 210 thereof. To deploy the delivery system 200, the strings 208 are temporarily threaded through the loop members 216 and through the eyelet 206 of the guide wire 204.

Both the strings 208 and the guide wire 204 are placed internally through the graft 202 and out the distal end 212 of graft 202. Either prior to or after the foregoing threading procedure, the graft 202 is inserted into a proximal end 218 of a very thin-walled sheath introducer 219 by radially compressing the stents 214 (if present). The graft 202 will remain seated in the sheath introducer 219 by virtue of the radial outward force imparted by the stents 214. As such, the sheath introducer 219 should be made of a material that is capable of resisting the expansive pressure of the compressed stents 214, yet should also have good bending compliance. Contemplated materials include very thin-walled polypropylene or polyethylene sheet stock e.g. having a thickness of about 1-5 mil. which will act as an outer skin-like barrier and stent retainer for the graft until placement. This arrangement is shown in FIG. 8a.

After the delivery system 200 is readied for deployment in the above-described manner, the proximal end 207 of the guide wire 204 is inserted into the femoral artery. It is advanced to the descending aorta, around the aortic arch, and then to the ascending aorta where the eyelet 206 of the guide wire 204 is positioned using an imaging device, such as an image amplifier, such that the proximal end 207 enters the aortic valve. The attached strings 208 are allowed to continuously pass through the loop members 216 of the graft 202 so that the graft 202 and the sheath introducer 219 remain in a stable position outside of the body during insertion and positioning of the guide wire 204 in the ascending aorta. With the guide wire 204 in position, the sheath introducer 219 with the graft 202 installed therein is inserted into the femoral artery. The guide wire 204 is held in constant position as the strings 208 are pulled. This movement of the strings 208 causes the sheath introducer 201 and the graft 202 to be hoisted towards the eyelet 206 of the guide wire 204. This moves the sheath introducer 219 and the graft 202 through the femoral artery, up to the descending aorta, around the aortic arch, and into the ascending aorta, until they are properly positioned. The sheath introducer 219 is then separated from the graft 202 and removed by pulling on its distal end while holding the strings 208 to keep the graft 202 in position. As the sheath introducer 219 is removed, the graft 202 is revealed, thus allowing stents 214 (if present) to expand and secure the graft 202 in position. After the sheath introducer 201 is completely removed, the strings 208 are detached from the loop members 203 of the graft 202 and the eyelet 206 of the guide wire 204 by pulling one end of each string until the opposing end is fully withdrawn from the body. After the strings 208 are removed, the guide wire 204 is also removed from the body.

FIG. 8b shows how the delivery system 200 in FIG. 8a can be used with an alternate aortic arch graft 251 and without a sheath introducer 219. The alternate graft 251 includes multiple loop members 252 placed around the outside of the graft and positioned near the center of expandable stents 254. Before deployment of the graft 251 in a body, the stents 254 are wrapped tightly by stent retaining members such as filament/strings 256, causing them to compress. Other stent retaining members, such as springs, could also be used. With the stents 254 in a compressed state, the filament/strings 256 are tied in a releasable slipknot 258 or the like, with its remaining length running along the outside of graft 251. The graft 251 is positioned in the aortic arch using the hoisting method as described above in FIG. 8a. The stents 254 are released by pulling one end of the filament/strings 256 until the slipknot 258 is released, thus allowing the stents 254 to expand. The filament/strings are then detached from the loop members 252 by pulling one end of each string until the opposing end is fully withdrawn from the body.

As previously stated, FIGS. 9a and 9b show how a modified version 220 of the aortic arch graft 20 of FIG. 3a can be deployed using the delivery system 200. The modification refers to the fact that the modified version 220 has loop members on its proximal end for hoisting. It should be noted that the guide wire 204 and the strings 208 could also be used to hoist a stentless version of the graft 202 with or without the use of the sheath introducer 219. In that case, stents would be inserted to secure the graft following its deployment in the aortic arch region.

Figure 10:
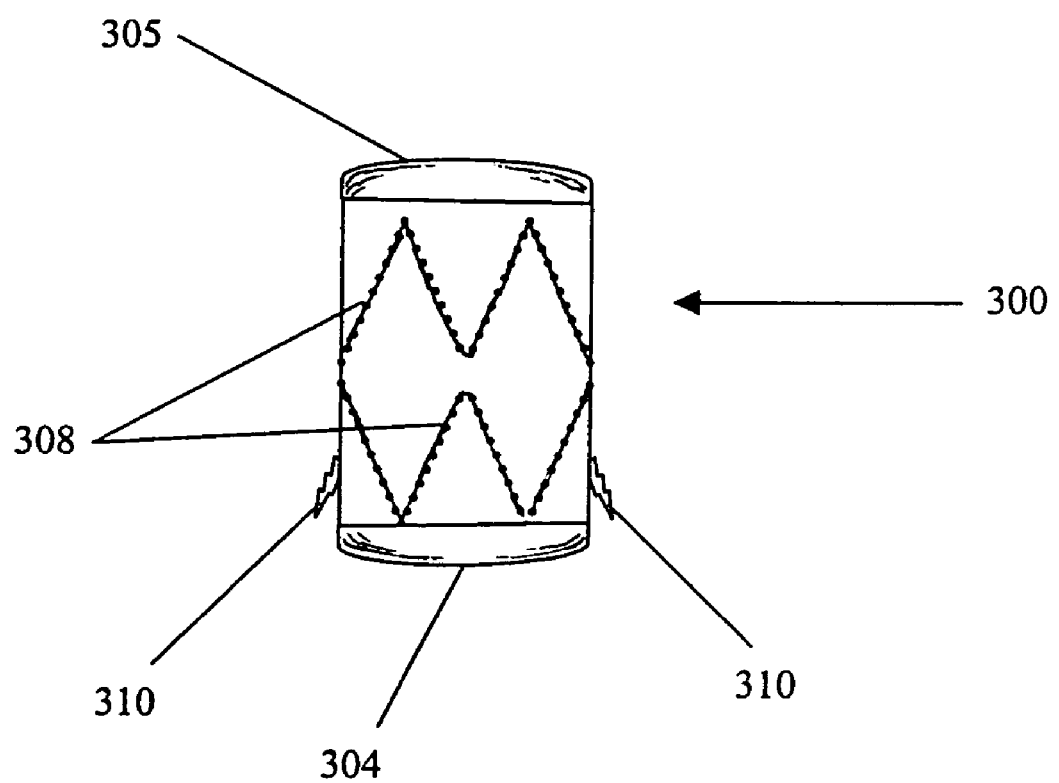
FIG. 10 is a side view of an occluder with integral anchor members.
Figure 11:
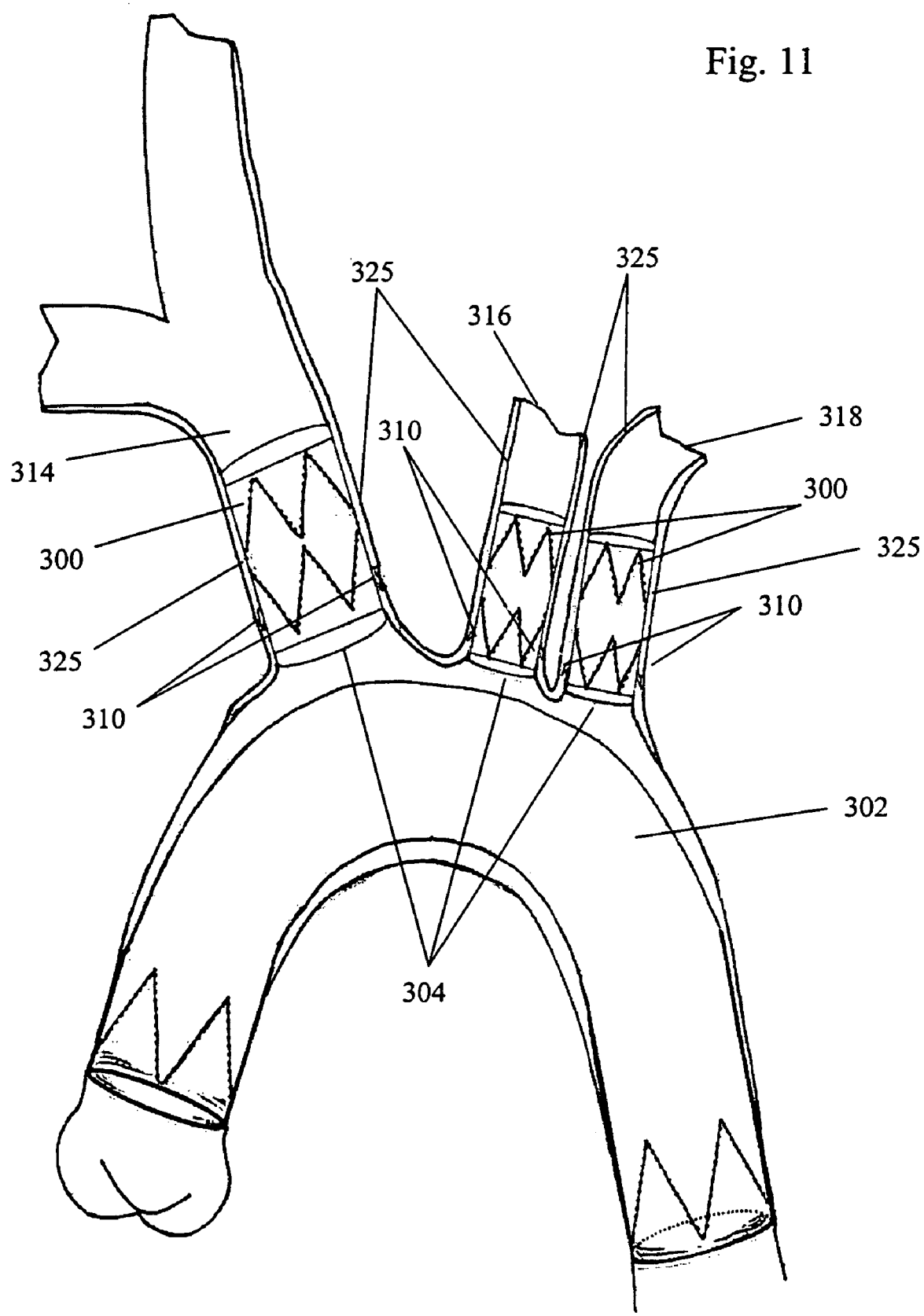
FIG. 11 is a perspective view showing three occluders according to FIG. 10 deployed in the branches of an aortic arch.

Turning to FIGS. 10 and 11, an exemplary occluder 300 is shown for use with a tubular aortic arch graft 302 that has no integral occluders. The occluder 300 has a tubular shape when in its expanded state and is capable of being folded or twisted for loading into a sheath introducer, such as the introducer 42 (or 58) of FIGS. 4a and 4b. The occluder 300 can be constructed of a suitable stent graft material, such as dacron. As shown in FIG. 10, the occluder 300 has a first closed (proximal) end 304 and a second closed (distal) end 305, with each end having a stent 308 secured thereto by sewing or the like. Alternatively, a single stent could be used. The occluders 300 are of a size to adequately block blood flow through an aortic arch artery when positioned therein. The occluder 300 further includes one or more (two are shown) integral anchor members 310, such as spikes, at one end thereof. The anchor members 310 are preferably sized to be long enough to enter the wall of an artery without piercing through the wall. FIG. 11 shows the positioned graft 302 in an aortic arch and three occluders 300 with anchor members 310 respectively positioned in the right innominate artery 314, the left carotid artery 316 and the left subclavian artery 318. The anchor members 310 are located at the proximal ends 304 of the occluders 300 and are anchored in the arterial walls 325. The occluders 300 may be introduced and properly positioned in accordance with a delivery system as seen in FIG. 4a or 4b, using carotid and subclavian approaches. Note that the three occluders 300 and the graft 302 shown in FIGS. 10 and 11 can be provided in kit form for use by a medical practitioner to exclude an aortic arch aneurysm. The kit could further include a sheath introducer as shown in FIG. 4a or 4b.

C. Branched Aortic Arch Graft

As indicated, one solution to the aortic arch repair problem is to implant a branched aortic arch graft without cutting off blood supply to the arteries leading from the aortic branches. Preferably, to avoid possible complications associated with deploying a branch using a carotid approach, the graft will only have two branches, one for the right innominate artery and the other for the left subclavian artery. As such, the left common carotid artery will be blocked from blood supply. Therefore, a carotid-subclavian bypass procedure and an occlusion of the left common carotid artery proximate to the aortic arch must be done to reintroduce blood flow to the left common carotid artery prior to graft introduction, as shown in FIG. 12. The entire exclusion operation, including bypass and graft deployment procedure, can be implemented by two teams of surgeons. A first surgical team performs a left carotid-subclavian bypass, in which a bypass graft 402 is placed between the left carotid artery 406 and the left subclavian artery 422. This is followed by an occlusion of the left common carotid artery 406 proximate to an aortic arch 408 by tying 410 or use of an occluder (see FIG. 10). A second surgical team exposes a femoral artery (not shown in FIG. 12) and a right brachial artery 430 and a left brachial artery 431 (see FIG. 13). The second surgical team introduces a guide wire 414a through a femoral artery, to the descending aorta 418, and around the aortic arch to the ascending aorta 419.

Similar procedures are performed relative to the two non-occluded aortic branches. Guide wire 414b is introduced through a femoral artery to the descending aorta 418, to the right innominate/right subclavian artery 420 and to the opening previously exposed in the right brachial artery 430. A guide wire 414c is introduced through a femoral artery to the descending aorta 418, to the left subclavian artery 422, and to the opening previously exposed in the left brachial artery 431. The second surgical team introduces deployments members such as strings/filaments 415 through the body to the openings in the right and left brachial arteries 430 and 431 using the same procedure as described above for the guide wires 414b and 414c. The guide wires 414a-c and strings/filaments 415 may all then be passed through a sheath introducer 460 so that the strings/filaments 415 can be attached to corresponding parts of a branched aortic arch graft 440 and the guide wires 14a-c can be used to guide the delivery system with the graft, as will now be described.

Turning to FIG. 13, a branched aortic arch graft 440 is shown with a delivery system 442 for positioning the graft 440. As indicated above, the graft 440 is constructed with two branches 444, one for the right innominate artery the other for the left subclavian artery. The graft may also have loop members 447 at a proximal end 450. The loop members 447 may be closed or partially open such that deployment members, such as strings/filaments 452 may be threaded or otherwise attached for the purpose of closing the proximal end 450 during graft deployment, as described below. The branches 444 each have an open ends 448. The end 448 may have loop members 447 mounted thereon so that strings/filaments 415 may be threaded or otherwise attached for the purpose of closing the open ends 448 during graft deployment. The delivery system 442 comprises a sheath introducer 460 and a catheter 462. The catheter 462 includes a tip 464 and first and second proximal expandable portions 466 and 468.

With reference now to FIGS. 14a, 14b, and 14c, loading of the graft 440 into the sheath introducer 460 is shown. First, the guide wires 414a-c and the strings 415 are passed through a sheath introducer 460 (see FIG. 14c). Next, a non-self deploying stent 469 is placed around the second proximal expandable portion 468 of the catheter 462 as seen in FIG. 14a. FIG. 14b shows the guide wires 414b and 414c from the brachial arteries placed through the open ends 448 of the branches 444 of the graft 440. FIG. 14b also shows the guide wire 414a from the ascending aorta being passed through the tip 464 of catheter. Next, the strings/filaments 415 are threaded through the loop members 447 at the distal ends of the branches 444 of the graft 440 and secured (e.g. with a releasable slipknot), and a string/filament 452 is threaded through the loop members 447 at the proximal end of the graft 440. The graft 440 is then placed over the catheter 462 until its proximal end reaches the first proximal expandable portion 466. FIG. 14c shows the next step where the string/filament 452 is pulled tightening the proximal end of the graft 440 around the proximal expandable portion 466 of the catheter 462. As shown in FIG. 14c, the catheter 462 and the graft 440 are then slid into the sheath introducer 460 until the catheter tip 464 reaches the proximal end of the sheath introducer 460.

Figure 15:
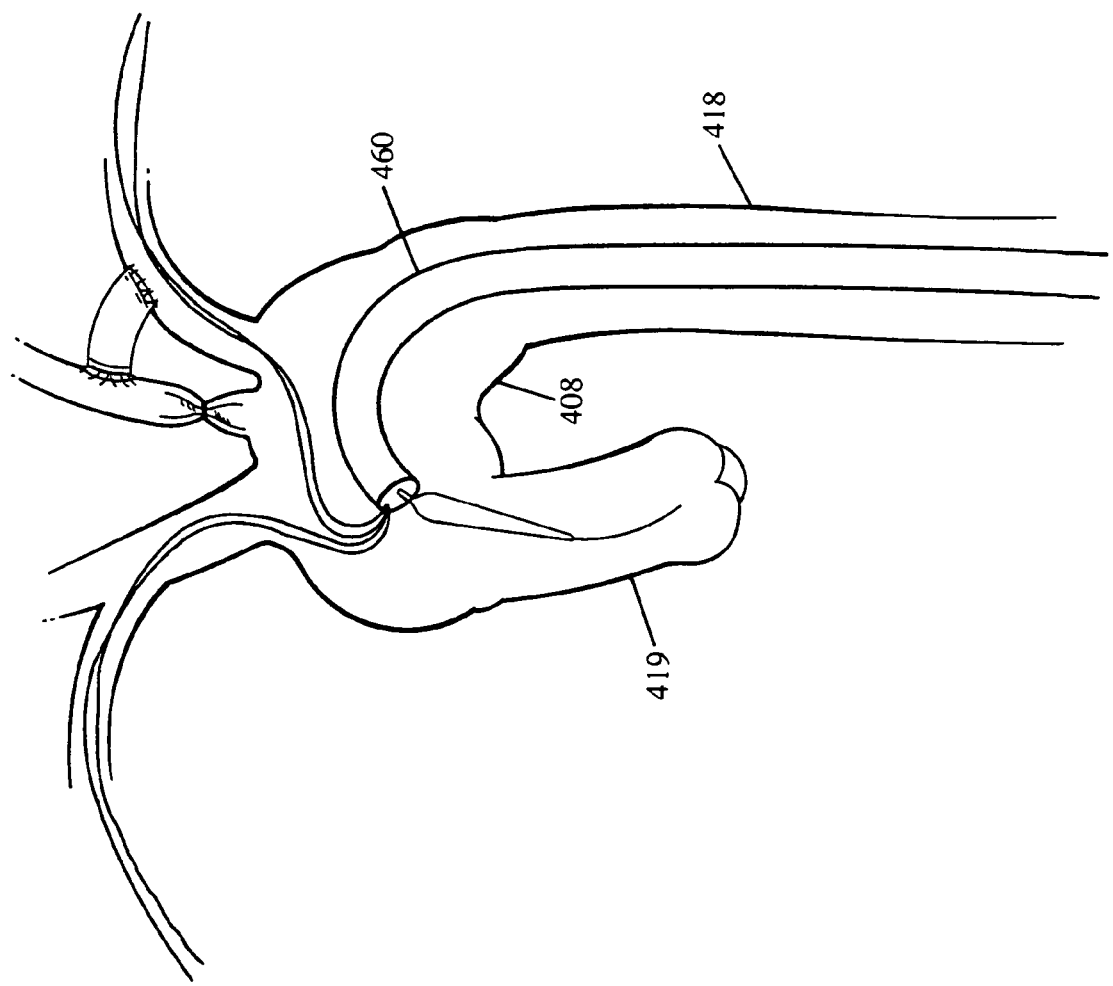
FIG. 15 is a perspective view of the delivery system of FIG. 13 deployed within an aortic arch and advancing into an ascending aorta.

FIG. 15 shows the sheath introducer 460, loaded as depicted in FIG. 14c following advancement into the aortic arch 408. This can be done in the manner described above by inserting the loaded sheath introducer 460 into the open femoral artery, passing it through the descending aorta 418, and then around the aortic arch 408 into the ascending aorta 419.

Figure 16:
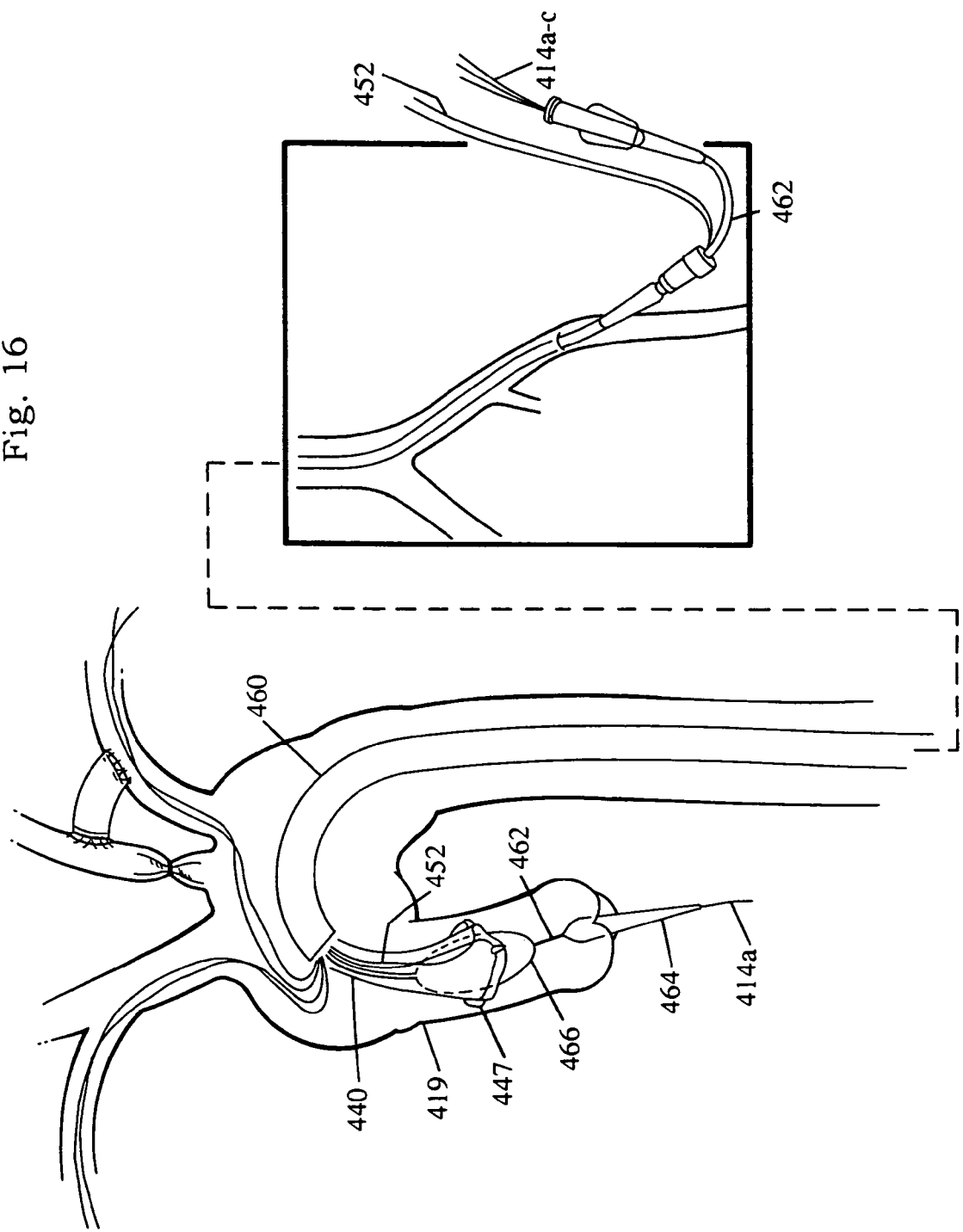
FIG. 16 is a two-part perspective view of the graft of FIG. 13 being deployed in an ascending aorta.
Figure 17:
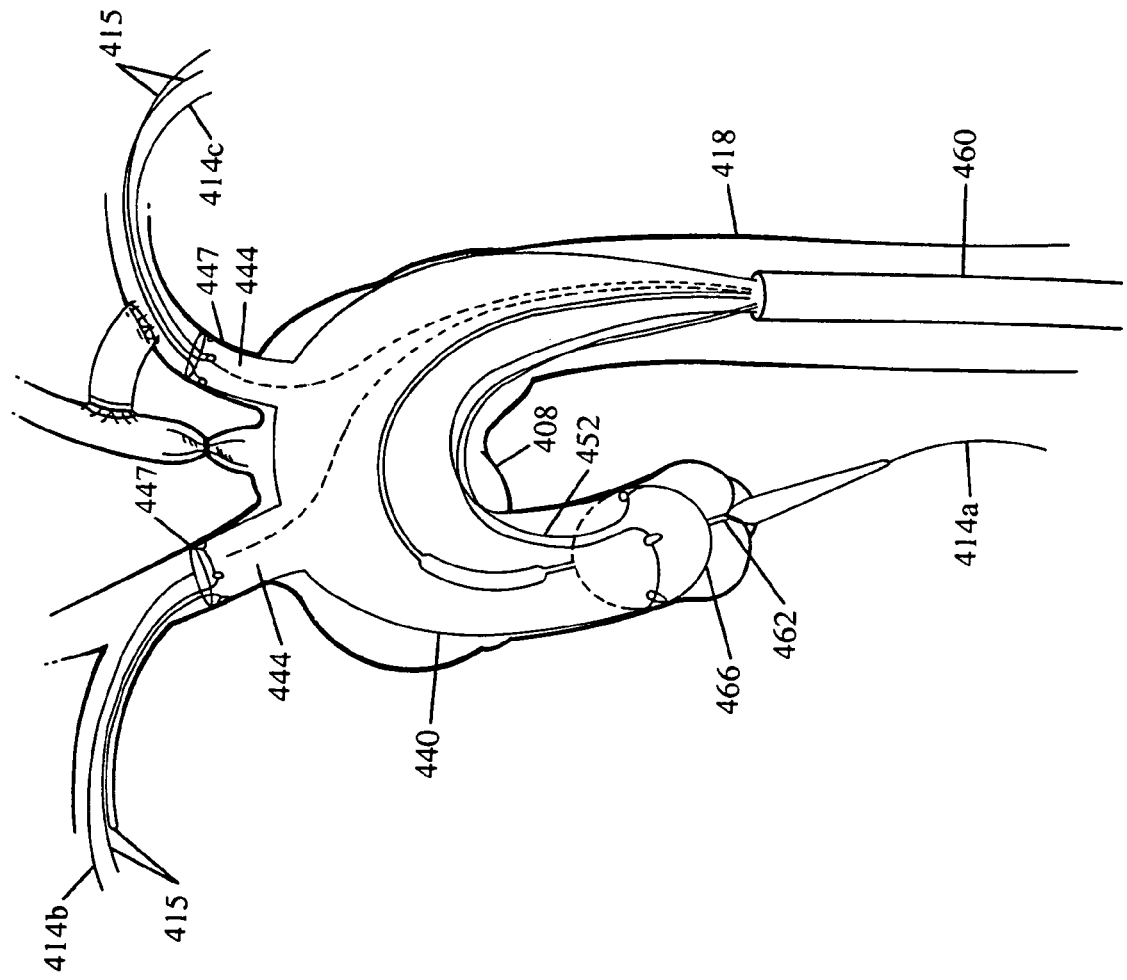
FIG. 17 is a perspective view of the branches of the graft of FIG. 13 being deployed in the branches of an aorta.

Turning to FIG. 16 and FIG. 17, the graft 440 is extracted from the sheath 460. Note that the first proximal expandable portion 466 of the catheter 462 is expanded tightly against the proximal end of the graft 440, which is closed by maintaining tension on the string/filament 452 threaded through the loop members 447. The graft 440 is pushed out of the sheath introducer 460 and into the ascending aorta 419 by proximally advancing the catheter 462 relative to the sheath introducer 460. When the graft 440 is in a desired position, the string/filament 452 is released and the first proximal expandable portion 466 of the catheter 462 is expanded until the graft 440 is tight against an arterial wall. This temporarily secures the graft 440 as the sheath introducer 460 is pulled down the descending aorta 418 until the graft 440 is fully exposed. Next, each branch 444 of the graft 440 is positioned into their respective aortic branch by pulling on the distal ends of the strings/filaments 415 threaded through the loop members 447 of the branch 444.

Figure 18:
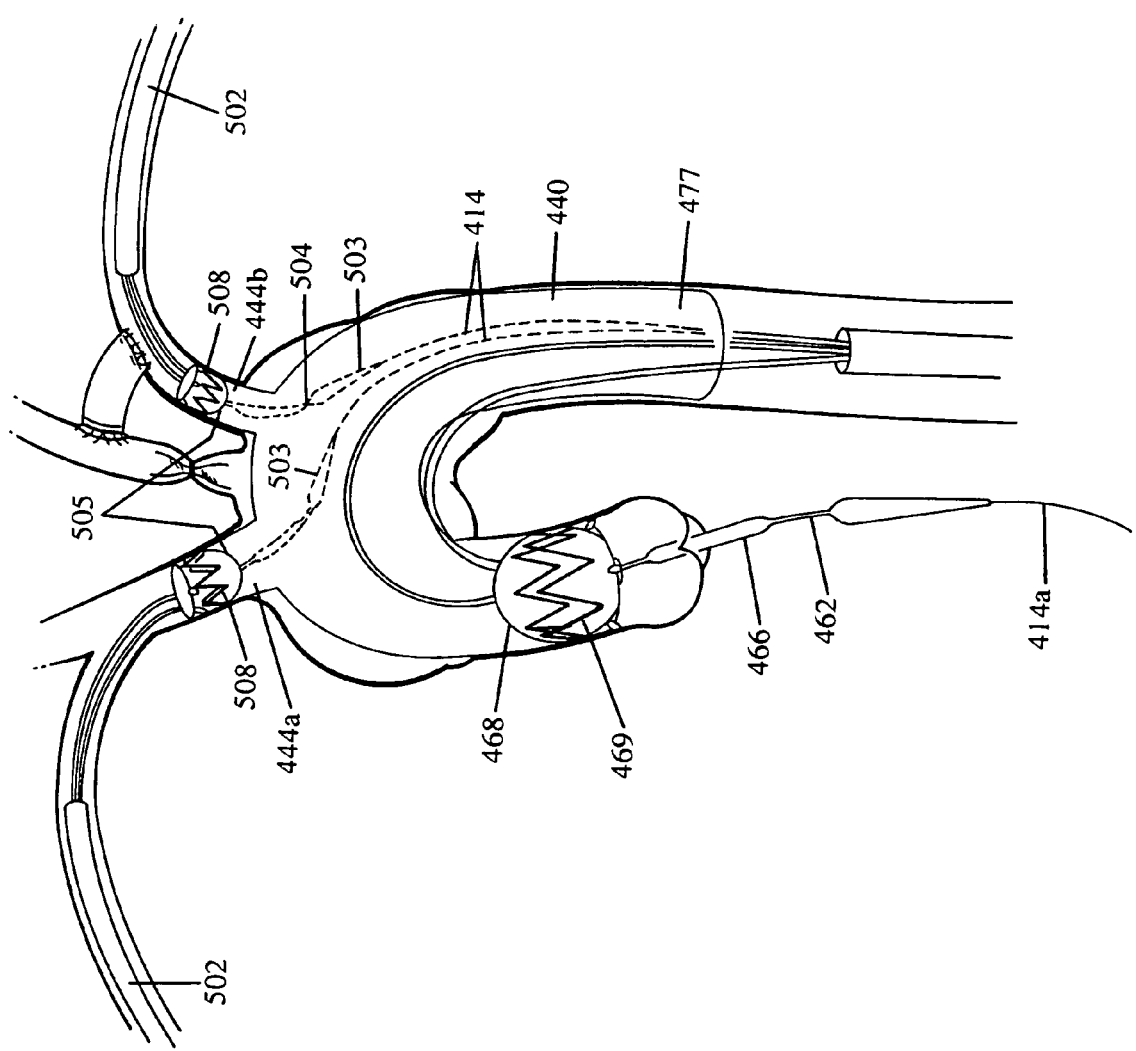
FIG. 18 is a perspective view of the graft of FIG. 13 being secured with stents in an aortic arch region and the branches of an aorta.

As shown in FIG. 18, with the graft 440 in position, the first proximal expandable portion 466 of the catheter 462 is deflated. The catheter 462 is pushed further until the second most proximal expandable portion 468 of the catheter 462 with the stent 469 is positioned at the end of the proximal end of the graft 440. The second proximal expandable portion 468 is then expanded, causing the stent 469 to open and secure the proximal end of the graft 440. The stent 469 may also be self-releasing, expanding as it is released from the sheath introducer 460. The branches 444 of the graft 440 are then secured in their respective aortic branches and the distal end 477 of the graft 440 in similar fashion as will now be described.

Figure 19:
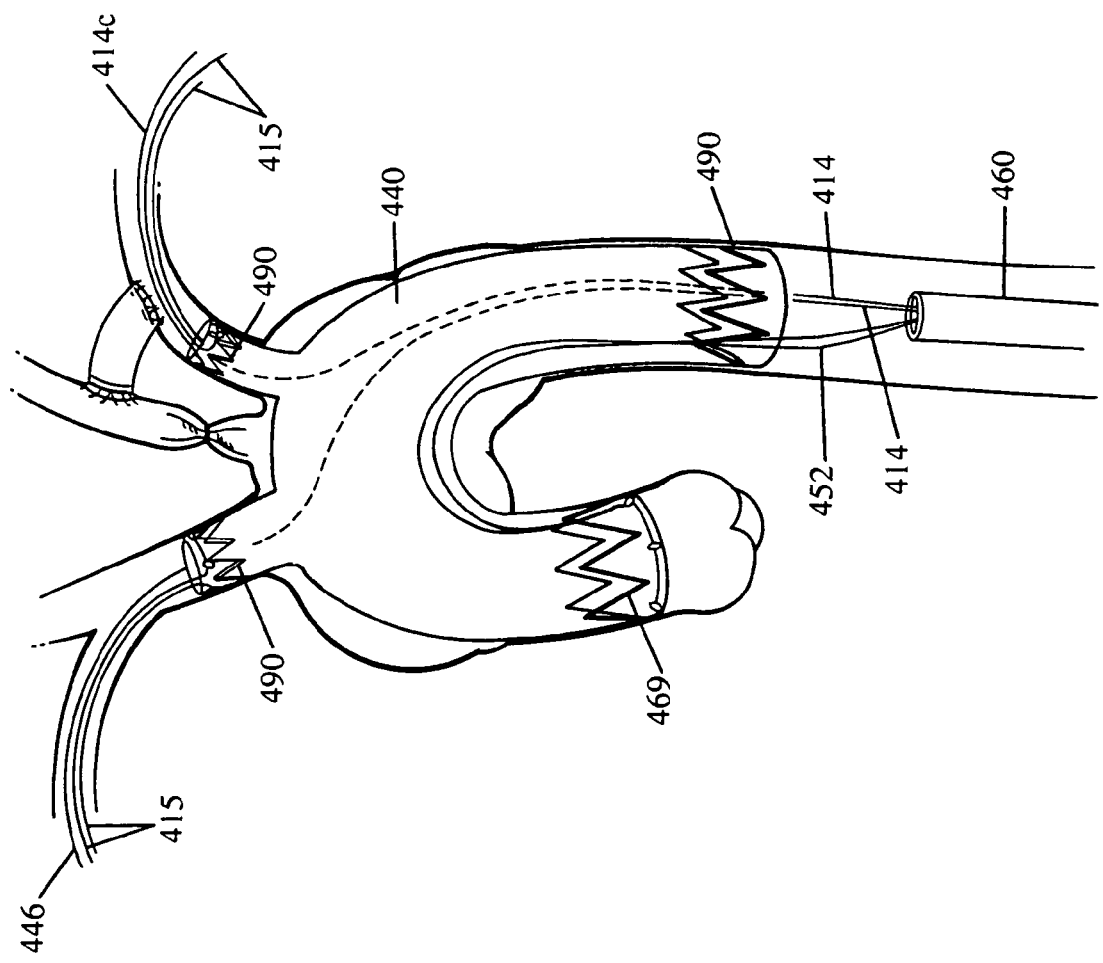
FIG. 19 is a perspective view of the graft of FIG. 13 secured in an aortic arch region and branches of an aorta and the delivery system of FIG. 13 being removed.

With reference to FIGS. 18 and 19, the branches of the graft are deployed using the same procedure as described above for the main body of the graft. The guide wires 414b and 414c are each passed through the catheter tip 503 of a respective delivery system 502. One of delivery systems 502 is then inserted into the open right brachial artery until it reaches the branch 444a of the graft 440 in a right innominate artery. The other delivery system 502 is inserted into the open left brachial artery until it reaches the branch 444b of the graft 440 in a left subclavian artery. Catheters 504 are pushed until the second most proximal expandable portions 505 thereof, each carrying a stent 508, are respectively positioned at the distal end of the branches 444a and 444b. The second proximal expandable portions 505 of each catheter 504 are then expanded causing the stents 508 to open and secure the respective distal end of the branches 444a and 444b. The delivery systems 502 are then removed from the body. Then, with the graft 440 secured by stents 469 and 508, the sheath introducer 460 is removed from the body, along with the strings/filaments 415 and 452, and the guide wires 414 by pulling on the distal ends.

Accordingly, a system and method for exclusion of an aneurysm of the ascending/descending aorta and/or the aortic arch have been disclosed. While various embodiments of the invention have been shown and described, it should be apparent that many variations and alternative embodiments could be implemented in accordance with the teachings herein. It is understood, therefore, that the invention is not to be in any way limited except in accordance with the spirit of the appended claims and their equivalents.

What is claimed is:

1. A delivery system for introducing an aortic arch graft into an aortic arch region via a femoral approach, comprising:
   a guide member having a distal end and a proximal end, said proximal end carrying a hoisting assembly;
   an aortic arch graft having a proximal end temporarily connected to said hoisting assembly;
   said guide member extending axially through an interior of said graft and extending from each end thereof;
   said hoisting assembly having a structure that includes a distal end accessible at said guide member distal end, a proximal end temporarily connected to said graft, a first medial portion spaced from said hoisting assembly proximal end and detachably carried by said guide member proximal end, a second medial portion spaced from said hoisting assembly first medial portion and extending along a length of said guide member through said graft interior to said hoisting assembly distal end, and said hoisting assembly structure enabling hoisting assembly operation by pulling said hoisting assembly distal end distally away from said guide member proximal end; and
   said hoisting assembly being arranged on said guide member proximal end so that said pulling of said hoisting assembly distal end distally away from said guide member proximal end effects a hoisting of said graft using said guide member as a hoist element that displaces said graft proximal end toward said guide member proximal end and away from said guide member distal end.

2. A delivery system in accordance with claim 1 wherein said graft further includes loop members around a proximal end of said graft that are temporarily connected to said hoisting assembly.

3. A delivery system in accordance with claim 1 wherein said aortic arch graft comprises a stent at each end of said graft, and wherein said delivery system further includes a sheath introducer having a soft bending compliant thin-wall sheath that receives said graft and compress said stents for delivery into a patient's body.

4. A delivery system in accordance with claim 1 wherein said aortic arch graft comprises:
   a stent at each end of said graft;
   loop members around an outside portion of said graft and positioned near said stents, said loop members positioning retaining members around said stents; and
   wherein said delivery system further includes:
   said retaining members compressing said stents during delivery of said graft into a patient's body, and said retaining members being remotely releasable from said graft to deploy said stent.

5. A delivery system in accordance with claim 4 wherein said retaining members comprise strings.

6. A delivery system in accordance with claim 5 wherein said strings are wrapped around said stent in a releasable slipknot, with said releasable slipknot being released from a distal end of said string outside a patient's body.

7. A delivery system for introducing an aortic arch graft into an aortic arch region via a femoral approach, comprising:
   a guide member having a distal end and a proximal end, said proximal end carrying a hoisting assembly;
   an aortic arch graft having a proximal end temporarily connected to said hoisting assembly;
   said guide member extending axially through an interior of said graft and extending from each end thereof;
   said hoisting assembly having a structure that includes a distal end accessible at said guide member distal end, a proximal end temporarily connected to said graft, a first medial portion spaced from said hoisting assembly proximal end and detachably carried by said guide member proximal end, a second medial portion spaced from said hoisting assembly first medial portion and extending along a length of said guide member through said graft interior to said hoisting assembly distal end, and said hoisting assembly structure enabling hoisting assembly operation by pulling said hoisting assembly distal end distally away from said guide member proximal end;

said hoisting assembly being arranged on said guide member proximal end so that said pulling of said hoisting assembly distal end distally away from said guide member proximal end effects a hoisting of said graft using said guide member as a hoist element that displaces said graft proximal end toward said guide member proximal end and away from said guide member distal end;

said graft having one or more openings for receiving a hoisting element; and said hoisting assembly comprising one or more hoisting elements that are each releasably connected to one of said openings by a fold formed by folding said hoisting elements upon themselves, said hoisting elements each further comprising two first medial elements that provide said hoisting assembly first medial portion and are detachably carried by said guide member proximal end serving as said hoist element, two second medial elements that provide said hoisting assembly second medial portion and extend along a length of said graft through said graft interior, and two distal end elements that provide said hoisting assembly distal end for controlling said graft.

8. A delivery system in accordance with claim 7 wherein said guide member comprises one of a guide wire having an eyelet for receiving said hoisting element first medial elements or a catheter adapted to carry said hoisting element first medial elements.

9. A delivery system in accordance with claim 7 wherein said hoisting elements comprise strings.

10. A delivery system in accordance with claim 7 wherein said graft comprises a thin walled tubular body having an outside diameter of at least about 28-32 millimeters for fitting inside an aortic arch.

11. A delivery system in accordance with claim 7 wherein said graft comprises branches.

12. A delivery system in accordance with claim 10 wherein said branches comprise openings for receiving a hoisting element.

13. A delivery system in accordance with claim 7 wherein openings comprise loop members.

14. A delivery system in accordance with claim 7 wherein said graft comprises stents.

15. A delivery system in accordance with claim 7 wherein said graft comprises a built-in single self-deploying occluder for occluding aortic branches.

16. A delivery system in accordance with claim 15 further including a support ring disposed at a base of said occluder.

17. A delivery system in accordance with claim 7 wherein said graft comprises multiple self-deploying occluders for occluding aortic branches.

18. A delivery system in accordance with claim 7 wherein said graft comprises built-in multiple manually deployable occluders for occluding aortic branches.

* * * * *